(12) United States Patent
Albrecht et al.

(10) Patent No.: US 11,536,716 B2
(45) Date of Patent: Dec. 27, 2022

(54) CELL BASED ASSAY FOR DETERMINING ANTIBODY OR LIGAND BINDING AND FUNCTION

(71) Applicant: Hoffmann-La Roche Inc., Little Falls, NJ (US)

(72) Inventors: Rosmarie Albrecht, Zurich (CH); Maria Amann, Duebendorf (CH); Christina Claus, Ennetbaden (CH); Sandra Grau-Richards, Birmensdorf (CH); Joerg Zielonka, Bachenbuelach (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 476 days.

(21) Appl. No.: 15/745,666

(22) PCT Filed: Jun. 21, 2016

(86) PCT No.: PCT/EP2016/064238
§ 371 (c)(1),
(2) Date: Jan. 17, 2018

(87) PCT Pub. No.: WO2016/207124
PCT Pub. Date: Dec. 29, 2016

(65) Prior Publication Data
US 2018/0356411 A1 Dec. 13, 2018

(30) Foreign Application Priority Data
Jun. 25, 2015 (EP) .................................. 15173929

(51) Int. Cl.
*G01N 33/542* (2006.01)
*G01N 33/68* (2006.01)
*G01N 33/50* (2006.01)

(52) U.S. Cl.
CPC ....... *G01N 33/542* (2013.01); *G01N 33/5008* (2013.01); *G01N 33/5023* (2013.01); *G01N 33/6854* (2013.01)

(58) Field of Classification Search
CPC ........... G01N 33/5008; G01N 33/5023; G01N 33/542; G01N 33/6854
USPC ...................................................... 435/7.21
See application file for complete search history.

(56) References Cited

U.S. PATENT DOCUMENTS

| 5,661,035 | A | * | 8/1997 | Tsien | .................. | C07D 209/08 |
| | | | | | | 435/173.4 |
| 7,582,416 | B2 | | 1/2009 | Migeotte et al. | | |
| 2005/0123563 | A1 | * | 6/2005 | Doranz | .............. | A61K 47/6901 |
| | | | | | | 424/204.1 |
| 2007/0122406 | A1 | * | 5/2007 | Chamberlain | ....... | C07K 16/465 |
| | | | | | | 424/144.1 |
| 2015/0024410 | A1 | | 1/2015 | Jaga et al. | | |
| 2015/0252073 | A1 | * | 9/2015 | Hahn | ..................... | A61K 38/07 |
| | | | | | | 514/18.8 |
| 2016/0024176 | A1 | * | 1/2016 | Damschroder | .. | C07K 14/70575 |
| | | | | | | 424/134.1 |

FOREIGN PATENT DOCUMENTS

| CN | 103959063 | A | | 7/2014 |
| WO | 99/055735 | | | 11/1999 |
| WO | WO2002045659 | | * | 6/2002 |
| WO | 03/047420 | A2 | | 12/2003 |
| WO | 03/047420 | A3 | | 12/2003 |

OTHER PUBLICATIONS

Smith (2012) J Biomol Screen 17:713-726 (Year: 2012).*
Devaux, B. (Apr. 25, 2013). "Applications of HTRF and Tag-lite Assays for HTP Antibody Screening," Slides *HTRF Symposium*, Redwood City, California, thirty-one pages.
Chen, F. et al. (2015). "A dark-to-bright reporter cell for classical swine fever virus infection," *Antiviral Research* 117:44-51.
Herbath, M. et al. (2014). "Exploiting fluorescence for multiplex immunoassays on protein microarrays," *Methods and Applications in Fluorescence* 2.
International Preliminary Report on Patentability dated Dec. 26, 2017, for PCT Patent Application No. PCT/EP2016/064238 filed on Jun. 21, 2016, eight pages.
International Search Report dated Aug. 16, 2016, for PCT Patent Application No. PCT/EP2016/064238 filed on Jun. 21, 2016, six pages.
Smith, A.J. et al. (2012). "Feasibility of Implementing Cell-Based Pathway Reporter Assays in Early High-Throughput Screening Assay Cascades for Antibody Drug Discovery," *Journal of Biomolecular Screening* 17(6):713-726.
Tonevitsky, A.G. et al. (1988). "A new approach to studies of cell-antibody interactions using fluorescent lipid probes," *Elsevier* 236(2):315-317.
Visintin, M. et al. (1999). "Selection of antibodies for intracellular function using a two-hybrid in vivo system," *Proceedings of the National Academy of Sciences, National Academy of Sciences* 96(21):11723-11728.
Degorce et al., "HTRF: A Technology Tailored for Drug Discovery—A Review of Theoretical Aspects and Recent Applications" Current Chemical Genomics 3:22-32 ( 2009).

* cited by examiner

*Primary Examiner* — Changhwa J Cheu
(74) *Attorney, Agent, or Firm* — Jonathan P. Aumais

(57) ABSTRACT

The present invention relates to a new cell based assay for combined determination of antibody or ligand binding and function in the same vial.

26 Claims, 14 Drawing Sheets

Specification includes a Sequence Listing.

SEQUENCE LISTING

<160> NUMBER OF SEQ ID NOS: 9

<210> SEQ ID NO 1
<211> LENGTH: 10
<212> TYPE: DNA
<213> ORGANISM: Artificial sequence
<220> FEATURE:
<223> OTHER INFORMATION: Artificial: DNA repeat 1

<400> SEQUENCE: 1
gggaatttcc        10

<210> SEQ ID NO 2
<211> LENGTH: 11
<212> TYPE: DNA
<213> ORGANISM: Artificial sequence
<220> FEATURE:
<223> OTHER INFORMATION: Artificial: DNA repeat 2

```
<400> SEQUENCE: 2
ggggactttc c                                                        11

<210> SEQ ID NO 3
<211> LENGTH: 10
<212> TYPE: DNA
<213> ORGANISM: Artificial sequence
<220> FEATURE:
<223> OTHER INFORMATION: Artificial: DNA repeat 3

<400> SEQUENCE: 3
gggactttcc                                                          10

<210> SEQ ID NO 4
<211> LENGTH: 9
<212> TYPE: DNA
<213> ORGANISM: Artificial sequence
<220> FEATURE:
<223> OTHER INFORMATION: Artificial: DNA repeat 4

<400> SEQUENCE: 4 gggacttcc                                                            9

<210> SEQ ID NO 5
<211> LENGTH: 11
<212> TYPE: DNA
<213> ORGANISM: Artificial sequence
<220> FEATURE:
<223> OTHER INFORMATION: Artificial: DNA repeat 5

<400> SEQUENCE: 5
attgtagcgt a                                                        11

<210> SEQ ID NO 6
<211> LENGTH: 52
<212> TYPE: DNA
<213> ORGANISM: Artificial sequence
<220> FEATURE:
<223> OTHER INFORMATION: Artificial: Response element 1

<400> SEQUENCE: 6
gggaatttcc ggggactttc cgggaatttc cggggacttt ccgggaattt cc           52

<210> SEQ ID NO 7
<211> LENGTH: 60
<212> TYPE: DNA
<213> ORGANISM: Artificial sequence
<220> FEATURE:
<223> OTHER INFORMATION: Artificial: Response element 2

<400> SEQUENCE: 7
gggaatttcc gggaatttcc gggaatttcc gggaatttcc gggaatttcc gggaatttcc   60

<210> SEQ ID NO 8
<211> LENGTH: 59
<212> TYPE: DNA
<213> ORGANISM: Artificial sequence
<220> FEATURE:
<223> OTHER INFORMATION: Artificial: Response element 3

<400> SEQUENCE: 8
gggacttccg ggactttccg ggactttccg ggacttccg ggactttccg ggactttcc     59

<210> SEQ ID NO 9
```

```
<211> LENGTH: 71
<212> TYPE: DNA
<213> ORGANISM: Artificial sequence
<220> FEATURE:
<223> OTHER INFORMATION: Artificial: Response element 4

<400> SEQUENCE: 9
gggactttcc attgtagcgt agggactttc cattgtagcg tagggctttc cattgtagcg    60
tagggctttc c                                                        71
```

CELL BASED ASSAY FOR DETERMINING ANTIBODY OR LIGAND BINDING AND FUNCTION

SEQUENCE LISTING

This application contains a Sequence Listing submitted via EFS-Web and hereby incorporated by reference in its entirety. Said ASCII copy, created on Jun. 25, 2018, is named P32944-US-SequenceListing.txt, and is 2,227 bytes in size.

CROSS REFERENCE TO RELATED APPLICATIONS

This application is a 371 application of International Application No. PCT/EP2016/064238, filed on Jun. 21, 2016, which claims priority to European Application No. 15173929.9 filed on Jun. 25, 2015, the contents of which are incorporated herein in their entirety by reference.

FIELD OF THE INVENTION

The present invention relates to a new cell based assay for determining antibody or ligand binding and function.

BACKGROUND

Chemotherapy is until now still one of the most commonly used treatments for cancer. However, as chemotherapeutic reagents target actively dividing cells, which is one characteristic of cancerous cells, also healthy dividing cells such as blood cells, cells in the intestine, mouth and hair are affected resulting in rather strong side effects. Scientists are continuously working on the improvement of the administration and combination of chemotherapeutic reagents to minimize those side effects. Additionally, antibody based therapies have evolved over the last 15 years and represent now a valuable combination or alternative to chemotherapeutic approaches in the treatment of hematological malignancies and solid tumors. Unlike chemotherapy, antibody therapies target specific antigens on cancer cells thus allowing a more side directed treatment thereby reducing the side effects on healthy tissue. In the process of developing an antibody-based therapeutic reagent, various assays are required to identify the best candidates to bring into clinical trials and eventually to the market. In a first early preclinical phase, the antibodies have to be generated and analyzed for their target-specificity, as well as their affinity to the target and functionality. Binding properties can be analyzed using various protein-protein interaction assays, such as FRET-based methods, Surface Plasmon Resonance (SPR), fluorescence-activated cell sorting (FACS) or Alpha Screen™. Functionality is generally tested in various cell-based assays designed to mimic the physiological situation as close as possible to identify the best candidates to be tested in animal models before entering clinical trials. These functional assays are commonly carried out using primary cells, tumor cell lines or reporter cells that are designed to express a reporter upon activation of a specific pathway.

Designing combination assays which allow assessment of binding and functionality at an early state in the development process of an antibody therapeutic molecule would be of great benefit.

The inventors of the present invention developed a novel assay which combines the assessment of binding and functionality of antibodies and antibody like constructs (e.g. ligands) in the same vial. This novel assay is useful for example for screening or characterization purposes.

This new assay represents a valuable tool for early screening for not only binding but also functionality which will allow identifying the best binders at an early stage in the development of the drug candidate.

SUMMARY

In one embodiment there is provided an in vitro assay for determining the binding and functionality of an antibody or a ligand specifically binding to a target antigen comprising the following steps
 i) providing cells which
  a) express the target antigen on their surface,
  b) are covalently or noncovalently labelled with an energy donor compound and
  c) comprise a reporter gene under the control of a response element of the target antigen
 ii) adding the antibody or ligand to be tested
 iii) measuring the binding to the target antigen by determining the energy transfer, wherein the energy acceptor compound is covalently or noncovalently conjugated either to the antibody to be tested or to a secondary antibody binding to the first antibody; and
 iv) determining functionality of the antibody or ligand by correlating the level of the expression of the reporter gene with the level of target antigen activation or inhibition.

In one embodiment the energy donor and acceptor compound are a fluorescent resonance energy transfer (FRET) energy donor and acceptor compound and the energy transfer determined in step iii) is fluorescent resonance energy transfer (FRET). In one embodiment the FRET is time resolved FRET.

In one embodiment the FRET energy donor compound is Terbium cryptate and/or the FRET energy acceptor compound is d2.

In one embodiment the energy donor and acceptor compound are a bioluminescence energy transfer (BRET) energy donor and acceptor compound and the energy transfer determined in step iii) is bioluminescence energy transfer (BRET).

In one embodiment the energy donor and acceptor compound are an alpha screen acceptor and donor bead and the energy transfer determined in step iii) is an energy transfer from a singlet oxygen to an thioxene derivative within the acceptor bead.

In one embodiment the binding to the target antigen and the functionality of the antibody are measured in the same vial.

In one embodiment the target antigen is covalently or noncovalently labelled with the energy donor compound.

In one embodiment the energy donor compound is covalently or noncovalently linked to wheat germ agglutinin (WGA).

In one embodiment the reporter gene is selected from a gene coding for a fluorescent protein or a gene coding for an enzyme whose catalytic activity can be detected.

In one embodiment the reporter gene is coding for green fluorescent protein (GFP) or luciferase.

In one embodiment the target antigen is a cell surface receptor.

In one embodiment steps iii) and iv) are performed consecutively or simultaneously.

In one embodiment the target antigen and the response element are part of the NF-κB pathway.

In one embodiment the response element comprises at least one DNA repeat with a DNA sequence of SEQ ID NO: 1, 2, 3, 4 or 5.

In one embodiment the response element comprises a DNA sequence of SEQ ID NO 6, 7, 8 or 9.

In one embodiment the assay comprises the preliminary step of transfection of the cells with an expression vector comprising the DNA sequence coding for the reporter gene under the control of the target antigen response element.

DETAILED DESCRIPTION OF EMBODIMENTS OF THE INVENTION

I. Definitions

Figure 1:
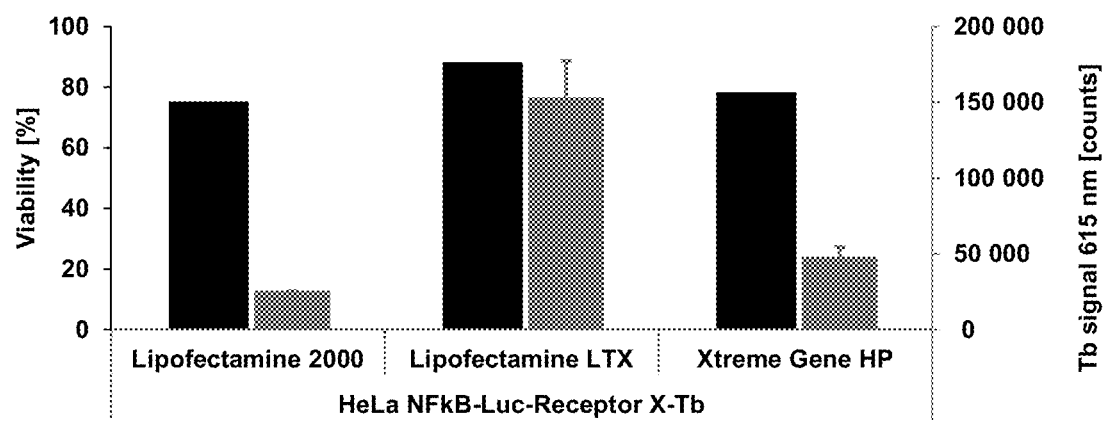
FIG. 1. Determination of the transfection efficiency as well as viability measurement of the cells after SNAP-Receptor X transfection and labeling with terbium, a donor fluorescent dye. The terbium signal was measured for 10 000 cells per well at a wavelength of 615 nm. The transfection reagents Lipofectamine 2000, Lipofectamine LTX and Xtreme Gene HP were compared.

As used herein, a "reporter gene" means a gene whose expression can be assayed. In one preferred embodiment a "reporter gene" is a gene that encodes a protein the production and detection of which is used as a surrogate to detect indirectly the activity of the antibody or ligand to be tested. The reporter protein is that protein encoded by the reporter gene. Preferably, the reporter gene encodes an enzyme whose catalytic activity can be detected by a simple assay method or a protein with a property such as intrinsic fluorescence so that expression of the reporter gene can be detected in a simple and rapid assay requiring minimal sample preparation. Non-limiting examples of enzymes whose catalytic activity can be detected are Luciferase, beta Galactosidase, Alkaline Phosphatase. Luciferase is a monomeric enzyme with a molecular weight (MW) of 61 kDa. It acts as a catalysator and is able to convert D-luciferin in the presence of Adenosine triphosphate (ATP) and Mg2+ to luciferyl adenylate. In addition, pyrophosphate (PPi) and adenosine monophosphate (AMP) are generated as byproducts. The intermediate luciferyl adenylate is then oxidized to oxyluciferin, carbon dioxide ($CO_2$) and light. Oxyluciferin is a bioluminescent product which can be quantitatively measured in a luminometer by the light released from the reaction. Luciferase reporter assays are commercially available and known in the art, e.g. Luciferase 1000 Assay System and ONE-Glo™ Luciferase Assay System.

The term "protein with intrinsic fluorescence" refers to a protein capable of forming a highly fluorescent, intrinsic chromophore either through the cyclization and oxidation of internal amino acids within the protein or via the enzymatic addition of a fluorescent co-factor. The term "protein with intrinsic fluorescence" includes wild-type fluorescent proteins and mutants that exhibit altered spectral or physical properties. The term does not include proteins that exhibit weak fluorescence by virtue only of the fluorescence contribution of non-modified tyrosine, tryptophan, histidine and phenylalanine groups within the protein. Proteins with intrinsic fluorescence are known in the art, e.g. green fluorescent protein (GFP), red fluorescent protein (RFP), Blue fluorescent protein (BFP, Heim et al. 1994, 1996), a cyan fluorescent variant known as CFP (Heim et al. 1996; Tsien 1998); a yellow fluorescent variant known as YFP (Oruro et al. 1996; Wachter et al. 1998); a violet-excitable green fluorescent variant known as Sapphire (Tsien 1998; Zapata-Hommer et al. 2003); and a cyan-excitable green fluorescing variant known as enhanced green fluorescent protein or EGFP (Yang et al. 1996) and can be measured e.g. by live cell imaging (e.g. Incucyte) or fluorescent spectrophotometry.

As used herein, the term "functionality of an antibody or ligand" refers to the biological activity of an antibody or ligand, e.g. the ability of an antibody or ligand to elicit a cellular response. For example through binding to a target antigen, the antibody activates or suppresses a cell signaling pathway, i.e. activates of inhibits the function of the target antigen. For example, the antibody to be tested binds to a receptor activating the NF-κB pathway and through this binding a response element in the cell nucleus is activated. When linking this response element to a reporter gene, the activation can be easily monitored in the assay of the invention. The term "functionality" also includes the effector functions of an antibody, e.g. C1q binding and complement dependent cytotoxicity (CDC); Fc receptor binding; antibody-dependent cell-mediated cytotoxicity (ADCC); antibody-dependent cellular phagocytosis (ADCP), cytokine secretion, immune complex-mediated antigen uptake by antigen presenting cells; down regulation of cell surface receptors (e.g. B cell receptor); and B cell activation.

As used herein "target antigen" refers to any cell surface antigen that can be targeted by an antibody or fragment thereof. It also refers to the receptor that can be targeted by a ligand. A "response element of the target antigen" refers to a specific transcription factor binding element, or cis acting element which can be activated or silenced on binding of a certain transcription factor. In one embodiment the response element is a cis-acting enhancer element located upstream of a minimal promotor (e.g. a TATA box promotor) which drives expression of the reporter gene upon transcription factor binding.

As used herein "NF-κB" refers to the "nuclear factor kappa-light-chain-enhancer of activated B cells" and is a transcription factor which is implicated in the regulation of many genes that code for mediators of apoptosis, viral replication, tumorigenesis, various autoimmune diseases and inflammatory responses. NFκB is present in almost all eukaryotic cells. Generally, it is located in the cytosol in an inactive state, since if forms a complex with inhibitory kappa B (IκB) proteins. Through the binding of ligands to integral membrane receptors (also referred to as "receptors of the NF-κB pathway", the IκB kinase (IKK) is activated. IKK is an enzyme complex which consists of two kinases and a regulatory subunit. This complex phosphorylates the IκB proteins, which leads to ubiquitination and therefore degradation of those proteins by the proteasome. Finally, the free NFκB is in an active state, translocates to the nucleus and binds to the KB DNA elements and induces transcription of target genes.

As used herein "NF-κB pathway" refers to the stimuli that lead to modulation of activity of NF-κB. For example activation of the Toll-like receptor signaling, TNF receptor signaling, T cell receptor and B cell receptor signaling through either binding of a ligand or an antibody result in activation of NF-κB. Subsequently, phosphorylated NF-κB dimers bind to KB DNA elements and induce transcription of target genes. Exemplary KB DNA elements useful herein are referred to as "response element of the NF-κB pathway". Hence, a "receptor of the NF-κB pathway" refers to a receptor which can trigger the modulation of activity of NF-κB: Examples of a "receptor of the NF-κB pathway" are Toll-like receptors, TNF receptors, T cell receptor and B cell receptor. Non-limiting examples of antibodies that upon binding to its target result in modulation of the activity of NF-κB are anti-CD40 antibodies, anti-DR5 antibodies, anti-DR4 antibodies, anti-41BB antibodies, anti-Ox40 antibodies and anti-GITR antibodies. Examples of ligands that upon binding to its target result in modulation of the activity of NF-κB are OX40 ligand, 4-1BB ligand or CD40 ligand.

"High-throughput screening" as used herein shall be understood to mean that a relatively large number of different antibody or ligand candidates can be analyzed for binding and functionality with the novel assay described therein. Typical such high-throughput screening is performed in multi-well microtiter plates, e.g. in a 96 well plate or a 384 well plate or a plates with 1536 or 3456 wells.

The term "energy donor compound" refers to a fluorescent resonance energy transfer (FRET) energy donor compound, a bioluminescence energy transfer (BRET) energy donor compound and an AlphaScreen donor bead. The term "energy acceptor compound" refers to a fluorescent resonance energy transfer (FRET) energy acceptor compound, a bioluminescence energy transfer (BRET) energy acceptor compound and an AlphaScreen acceptor bead.

The term "FRET" refers to fluorescent resonance energy transfer processes that occur between two chromophores. The chromophores as used herein comprise, for example, fluorescent, luminescent and other non-fluorescent components. "FRET," "fluorescence resonance energy transfer," "Förster resonance energy transfer" and "resonance energy transfer" are used interchangeably herein.

The term "time-resolved FRET" as used herein refers to energy transfer processes that occur between two chromophores based on time-resolved detection of the emission of the acceptor fluorophor (Morrison, L. E., 1988. Anal. Biochem., 174 (1) 101).

"FRET energy donor compound" also referred to as "FRET donor" or "FRET energy donor" as used herein refers to a donor fluorophore useful in FRET, and are known in the art. Non-limiting examples of energy donor compounds are listed in table B. Preferably the FRET energy donor compound is a rare earth element, like for example Terbium cryptate ("Lumi4-Tb") and Europium cryptates (Eu3+cryptate). Suitable lanthanide chelates useful in the method include those described for example in U.S. Pat. Nos. 5,622,821, 5,639,615, 5,656,433 and 4,822,733.

"FRET energy acceptor compound" also referred to as "FRET acceptor" or "FRET energy acceptor" as used herein refers to an acceptor fluorophore useful in FRET, and are known in the art, e.g. Alexa fluor dyes (Life technologies) or Cy5, YFP, FITC, chemically modified allophycocyanine (XL665), d2. Further non-limiting examples of energy acceptor compounds are listed in table B. Preferably the FRET energy acceptor compound is d2.

The term "BRET" refers to Resonance Energy Transfer (RET) between a bioluminescent donor moiety (i.e. a BRET energy donor compound) and a fluorescent acceptor moiety (i.e. a BRET energy acceptor compound).

The term "AlphaScreen" refers to Amplified Luminescent Proximity Homogeneous Assay and has been described e.g. in "Luminescent oxygen channeling immunoassay: Measurement of particle binding kinetics by chemiluminescence." Ullman, E F, et al. Proc. Natl. Acad. Sci. USA, Vol. 91, pp. 5426-5430, June 1994.

"Affinity" refers to the strength of the sum total of noncovalent interactions between a single binding site of a molecule (e.g., an antibody or ligand) and its binding partner (e.g., an antigen or a receptor). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

As used herein, the term "ligand" refers to any molecule that is able to bind to another molecule. Example of ligand molecules include, but are not limited to peptides, proteins, carbohydrates, lipids, or nucleic acids. Preferred ligands to be analysed with the assay described herein are peptides or proteins that are capable of binding to a target antigen. Usually such target antigen is a cell surface receptor.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies, cross-Fab fragments; linear antibodies; single-chain antibody molecules (e.g. scFv); and multispecific antibodies formed from antibody fragments. scFv antibodies are, e.g. described in Houston, J. S., Methods in Enzymol. 203 (1991) 46-96). In addition, antibody fragments comprise single chain polypeptides having the characteristics of a VH domain, namely being able to assemble together with a VL domain, or of a VL domain, namely being able to assemble together with a VH domain to a functional antigen binding site and thereby providing the antigen binding property of full length antibodies.

As used herein, "Fab fragment" refers to an antibody fragment comprising a light chain fragment comprising a VL domain and a constant domain of a light chain (CL), and a VH domain and a first constant domain (CH1) of a heavy chain.

The term "immunoglobulin molecule" refers to a protein having the structure of a naturally occurring antibody. For example, immunoglobulins of the IgG class are heterotetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a constant light (CL) domain, also called a light chain constant region. The heavy chain of an immunoglobulin may be assigned to one of five types, called α (IgA), δ (IgD), ε (IgE), γ (IgG), or μ (IgM), some of which may be further divided into subtypes, e.g. $\gamma_1$ (IgG$_1$), $\gamma_2$ (IgG$_2$), $\gamma_3$ (IgG$_3$), $\gamma_4$ (IgG$_4$), $\alpha_1$ (IgA$_1$) and $\alpha_2$ (IgA$_2$). The light chain of an immunoglobulin may be assigned to one of two types, called kappa (κ) and lambda (λ), based on the amino acid sequence of its constant domain. An immunoglobulin essentially consists of two Fab molecules and an Fc domain, linked via the immunoglobulin hinge region.

The term "antigen binding domain" refers to the part of an antigen binding molecule that comprises the area which specifically binds to and is complementary to part or all of an antigen. Where an antigen is large, an antigen binding molecule may only bind to a particular part of the antigen, which part is termed an epitope. An antigen binding domain may be provided by, for example, one or more antibody variable domains (also called antibody variable regions). Preferably, an antigen binding domain comprises an antibody light chain variable region (VL) and an antibody heavy chain variable region (VH).

The term "chimeric" antibody refers to an antibody in which a portion of the heavy and/or light chain is derived from a particular source or species, while the remainder of the heavy and/or light chain is derived from a different source or species, usually prepared by recombinant DNA techniques. Chimeric antibodies comprising a rabbit variable region and a human constant region are preferred. Other preferred forms of "chimeric antibodies" encompassed by the present invention are those in which the constant region has been modified or changed from that of the original antibody to generate the properties according to the invention, especially in regard to C1q binding and/or Fc receptor (FcR) binding. Such chimeric antibodies are also referred to as "class-switched antibodies". Chimeric antibodies are the product of expressed immunoglobulin genes comprising DNA segments encoding immunoglobulin variable regions and DNA segments encoding immunoglobulin constant regions. Methods for producing chimeric antibodies involve conventional recombinant DNA and gene transfection techniques are well known in the art. See e.g. Morrison, S. L., et al., Proc. Natl. Acad. Sci. USA 81 (1984) 6851-6855; U.S. Pat. Nos. 5,202,238 and 5,204,244.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); antibody-dependent cellular phagocytosis (ADCP), cytokine secretion, immune complex-mediated antigen uptake by antigen presenting cells; down regulation of cell surface receptors (e.g. B cell receptor); and B cell activation.

As used herein, the terms "engineer, engineered, engineering", are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches.

The term "amino acid mutation" as used herein is meant to encompass amino acid substitutions, deletions, insertions, and modifications. Any combination of substitution, deletion, insertion, and modification can be made to arrive at the final construct, provided that the final construct possesses the desired characteristics, e.g., reduced binding to an Fc receptor, or increased association with another peptide. Amino acid sequence deletions and insertions include amino- and/or carboxy-terminal deletions and insertions of amino acids. Particular amino acid mutations are amino acid substitutions. For the purpose of altering e.g. the binding characteristics of an Fc region, non-conservative amino acid substitutions, i.e. replacing one amino acid with another amino acid having different structural and/or chemical properties, are particularly preferred. Amino acid substitutions include replacement by non-naturally occurring amino acids or by naturally occurring amino acid derivatives of the twenty standard amino acids (e.g. 4-hydroxyproline, 3-methylhistidine, ornithine, homoserine, 5-hydroxylysine). Amino acid mutations can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful. Various designations may be used herein to indicate the same amino acid mutation. For example, a substitution from proline at position 329 of the Fc domain to glycine can be indicated as 329G, G329, $G_{329}$, P329G, or Pro329Gly.

An "effective amount" of an agent, e.g., a pharmaceutical formulation, refers to an amount effective, at dosages and for periods of time necessary, to achieve the desired therapeutic or prophylactic result.

The term "Fc domain" or "Fc region" herein is used to define a C-terminal region of an immunoglobulin heavy chain that contains at least a portion of the constant region. The term includes native sequence Fc regions and variant Fc regions. Although the boundaries of the Fc region of an IgG heavy chain might vary slightly, the human IgG heavy chain Fc region is usually defined to extend from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991. A "subunit" of an Fc domain as used herein refers to one of the two polypeptides forming the dimeric Fc domain, i.e. a polypeptide comprising C-terminal constant regions of an immunoglobulin heavy chain, capable of stable self-association. For example, a subunit of an IgG Fc domain comprises an IgG CH2 and an IgG CH3 constant domain.

A "modification promoting the association of the first and the second subunit of the Fc domain" is a manipulation of the peptide backbone or the post-translational modifications of an Fc domain subunit that reduces or prevents the association of a polypeptide comprising the Fc domain subunit with an identical polypeptide to form a homodimer. A modification promoting association as used herein particularly includes separate modifications made to each of the two Fc domain subunits desired to associate (i.e. the first and the second subunit of the Fc domain), wherein the modifications are complementary to each other so as to promote association of the two Fc domain subunits. For example, a modification promoting association may alter the structure or charge of one or both of the Fc domain subunits so as to make their association sterically or electrostatically favorable, respectively. Thus, (hetero)dimerization occurs between a polypeptide comprising the first Fc domain subunit and a polypeptide comprising the second Fc domain subunit, which might be non-identical in the sense that further components fused to each of the subunits (e.g. antigen binding moieties) are not the same. In some embodiments the modification promoting association comprises an amino acid mutation in the Fc domain, specifically an amino acid substitution. In a particular embodiment, the modification promoting association comprises a separate amino acid mutation, specifically an amino acid substitution, in each of the two subunits of the Fc domain.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. As also mentioned for chimeric and humanized antibodies according to the invention the term "human antibody" as used herein also comprises such antibodies which are modified in the constant region to generate the properties according to the invention, especially in regard to C1q binding and/or FcR binding, e.g. by "class switching" i.e. change or mutation of Fc parts (e.g. from IgG1 to IgG4 and/or IgG1/IgG4 mutation.)

The term "recombinant human antibody", as used herein, is intended to include all human antibodies that are prepared, expressed, created or isolated by recombinant means, such as antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

The term "hypervariable region" or "HVR," as used herein refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest*, 5th Ed. Public Health Service, National Institutes of Health, Bethesda, Md. (1991).) Hypervariable regions (HVRs) are also referred to as complementarity determining regions (CDRs), and these terms are used herein interchangeably in reference to portions of the variable region that form the antigen binding regions. This particular region has been described by Kabat et al., U.S. Dept. of Health and Human Services, "Sequences of Proteins of Immunological Interest" (1983) and by Chothia et al., *J. Mol. Biol.* 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table A as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE A

CDR Definitions[1]

| CDR | Kabat | Chothia | AbM[2] |
|---|---|---|---|
| $V_H$ CDR1 | 31-35 | 26-32 | 26-35 |
| $V_H$ CDR2 | 50-65 | 52-58 | 50-58 |
| $V_H$ CDR3 | 95-102 | 95-102 | 95-102 |
| $V_L$ CDR1 | 24-34 | 26-32 | 24-34 |
| $V_L$ CDR2 | 50-56 | 50-52 | 50-56 |
| $V_L$ CDR3 | 89-97 | 91-96 | 89-97 |

[1]Numbering of all CDR definitions in Table A is according to the numbering conventions set forth by Kabat et al. (see below).
[2]"AbM" with a lowercase "b" as used in Table A refers to the CDRs as defined by Oxford Molecular's "AbM" antibody modeling software.

Kabat et al. also defined a numbering system for variable region sequences that is applicable to any antibody. One of ordinary skill in the art can unambiguously assign this system of "Kabat numbering" to any variable region sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody variable region are according to the Kabat numbering system.

With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"No substantial cross-reactivity" means that a molecule (e.g., an antibody) does not recognize or specifically bind an antigen different from the actual target antigen of the molecule (e.g. an antigen closely related to the target antigen), particularly when compared to that target antigen. For example, an antibody may bind less than about 10% to less than about 5% to an antigen different from the actual target antigen, or may bind said antigen different from the actual target antigen at an amount consisting of less than about 10%, 9%, 8% 7%, 6%, 5%, 4%, 3%, 2%, 1%, 0.5%, 0.2%, or 0.1%, preferably less than about 2%, 1%, or 0.5%, and most preferably less than about 0.2% or 0.1% antigen different from the actual target antigen.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W. H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "antigen-binding site of an antibody" when used herein refer to the amino acid residues of an antibody which are responsible for antigen-binding. The antigen-binding portion of an antibody comprises amino acid residues from the "complementary determining regions" or "CDRs". "Framework" or "FR" regions are those variable domain regions other than the hypervariable region residues as herein defined. Therefore, the light and heavy chain variable domains of an antibody comprise from N- to C-terminus the domains FR1, CDR1, FR2, CDR2, FR3, CDR3, and FR4.

Especially, CDR3 of the heavy chain is the region which contributes most to antigen binding and defines the antibody's properties. CDR and FR regions are determined according to the standard definition of Kabat et al., Sequences of Proteins of Immunological Interest, 5th ed., Public Health Service, National Institutes of Health, Bethesda, Md. (1991) and/or those residues from a "hypervariable loop".

Antibody specificity refers to selective recognition of the antibody for a particular epitope of an antigen. Natural antibodies, for example, are monospecific.

The term "monospecific" antibody as used herein denotes an antibody that has one or more binding sites each of which bind to the same epitope of the same antigen.

The term "bispecific" antibody as used herein denotes an antibody that has at least two binding sites each of which bind to different epitopes of the same antigen or a different antigen. Techniques for making multispecific antibodies include, but are not limited to, recombinant co-expression of two immunoglobulin heavy chain-light chain pairs having different specificities (see Milstein and Cuello, Nature 305: 537 (1983)), WO 93/08829, and Traunecker et al., EMBO J. 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004); cross-linking two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., J. Immunol., 148(5):1547-1553 (1992)); using "diabody" technology for making bispecific antibody fragments (see, e.g., Hollinger et al., Proc. Natl. Acad. Sci. USA, 90:6444-6448 (1993)); and using single-chain Fv (sFv) dimers (see, e.g. Gruber et al., J. Immunol., 152:5368 (1994)); and preparing trispecific antibodies as described, e.g., in Tutt et al. J. Immunol. 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" (see, US 2008/0069820, for example).

The term "valent" as used within the current application denotes the presence of a specified number of binding sites in an antibody molecule. As such, the terms "bivalent", "tetravalent", and "hexavalent" denote the presence of two binding sites, four binding sites, and six binding sites, respectively, in an antibody molecule. The bispecific antibodies according to the invention are at least "bivalent" and may be "trivalent" or "multivalent" (e.g. "tetravalent" or "hexavalent").

Antibodies of the present invention have two or more binding sites and are bispecific. That is, the antibodies may be bispecific even in cases where there are more than two binding sites (i.e. that the antibody is trivalent or multivalent). Bispecific antibodies of the invention include, for example, multivalent single chain antibodies, diabodies and triabodies, as well as antibodies having the constant domain structure of full length antibodies to which further antigen-binding sites (e.g., single chain Fv, a VH domain and/or a VL domain, Fab, or (Fab)2) are linked via one or more peptide-linkers. The antibodies can be full length from a single species, or be chimerized or humanized.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "amino acid" as used within this application denotes the group of naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

As used herein, the expressions "cell", "cell line", and "cell culture" are used interchangeably and all such designations include progeny. Thus, the words "transfectants" and "transfected cells" include the primary subject cell and cultures derived there from without regard for the number of transfers. It is also understood that all progeny may not be precisely identical in DNA content, due to deliberate or inadvertent mutations. Variant progeny that have the same function or biological activity as screened for in the originally transformed cell are included.

"Affinity" refers to the strength of the sum total of noncovalent interactions between a single binding site of a molecule (e.g., an antibody or ligand) and its binding partner (e.g., an antigen). Unless indicated otherwise, as used herein, "binding affinity" refers to intrinsic binding affinity which reflects a 1:1 interaction between members of a binding pair (e.g., antibody and antigen/ligand and receptor). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

As used herein, the term "binding" or "specifically binding" refers to the binding of the antibody to an epitope of the antigen or the binding of a ligand to a receptor in an in-vitro assay, preferably by fluorescence resonance energy transfer (FRET).

The term "epitope" includes any polypeptide determinant capable of specific binding to an antibody. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody.

As used herein, the terms "engineer, engineered, engineering," particularly with the prefix "glyco-," as well as the term "glycosylation engineering" are considered to include any manipulation of the glycosylation pattern of a naturally occurring or recombinant polypeptide or fragment thereof. Glycosylation engineering includes metabolic engineering of the glycosylation machinery of a cell, including genetic manipulations of the oligosaccharide synthesis pathways to achieve altered glycosylation of glycoproteins expressed in cells. Furthermore, glycosylation engineering includes the effects of mutations and cell environment on glycosylation. In one embodiment, the glycosylation engineering is an alteration in glycosyltransferase activity. In a particular embodiment, the engineering results in altered glucosaminyltransferase activity and/or fucosyltransferase activity.

II. Novel Assay

The inventors developed an assay that is suitable for a high-throughput format (384 well) which enables combined analysis of antibody or ligand binding and functionality in one well or vial. Functionality of the antibody or ligand (e.g. the biological activity of an antibody or ligand, e.g. the ability of an antibody or ligand to elicit a cellular response, for example to activate or inhibit the target antigen) is evaluated by using transfected reporter cell lines which have a reporter gene expressed upon activation of a response element. In one embodiment said reporter gene is selected from a gene encoding for a fluorescent protein (e.g. green fluorescent protein, GFP) and/or a gene encoding for an enzyme whose catalytic activity can be detected (e.g. Luciferase). To address the binding, a cell-based FRET method, BRET or AlphaScreen are applied.

In one embodiment there is provided an in vitro assay for determining the binding and functionality of an antibody or a ligand specifically binding to a target antigen comprising the following steps
i) providing cells which
   a) express the target antigen on their surface,
   b) are covalently or noncovalently labelled with an energy donor compound and
   c) comprise a reporter gene under the control of a response element of the target antigen
ii) adding the antibody or ligand to be tested
iii) measuring the binding to the target antigen by determining the energy transfer, wherein the energy acceptor compound is covalently or noncovalently conjugated either to the antibody to be tested or to a secondary antibody binding to the first antibody; and
iv) determining functionality of the antibody or ligand by correlating the level of the expression of the reporter gene with the level of target antigen activation or inhibition.

In one embodiment the energy donor and acceptor compound are a fluorescent resonance energy transfer (FRET) energy donor and acceptor compound and the energy transfer determined in step iii) is fluorescent resonance energy transfer (FRET). In one embodiment the FRET is time resolved FRET.

A technology to study protein-protein interactions in a microplate format is the time-resolved FRET. Time-resolved fluorescence resonance energy transfer (TR-FRET) applications are based on energy transfer between a donor and an acceptor molecule. FRET is a non-radiative energy transfer from a fluorescent donor molecule to an appropriate acceptor molecule. When a donor molecule is excited by a light source, it produces fluorescence. If an acceptor molecule is in close proximity, and the emission spectrum of the donor molecule overlaps with the excitation spectrum of the acceptor molecule, the donor molecule, instead of emitting fluorescent light, can transfer its excitation energy to the acceptor molecule. The acceptor molecule will then emit fluorescence at the acceptor emission wavelength. The apparition of fluorescent light at the acceptor emission wavelength indicates that the donor and acceptor molecules are in close proximity to each other as the donor and acceptor molecules need to be less than about 20 nm apart for energy transfer to occur, e.g., 5-10 nm apart. Typically, close proximity between the donor and acceptor molecules is achieved via bioaffinity interactions, e.g., protein-protein binding, antigen-antibody binding, ligand-receptor binding, DNA hybridization, and DNA-protein binding.

A large variety of donor and acceptor molecules exist. Typically the donor and acceptor molecules used in FRET assays are fluorophores that have short half-lives. The performance of traditional FRET chemistries can be reduced by background fluorescence from sample components such as buffers, proteins, chemical compounds, and cell lysate. Detected fluorescence intensities must be corrected for this auto-fluorescence, which reduces assay sensitivity and can complicate result interpretation. This type of background fluorescence is transient (with a lifetime in the nanosecond range) and can therefore be eliminated using time-resolved methodologies.

TR-FRET takes advantage of the unique properties of lanthanide ions such as europium (Eu), terbium (Tb), samarium (Sm), and dysprosium (Dy) ions. Because of their specific photophysical and spectral properties, complexes of rare earth ions are of interest for fluorescence applications in biology. Specifically, they have large Stoke's shifts and long emission half-lives (from μsec to msec) when compared to more traditional fluorophores.

FRET energy acceptors are commercially available at PerkinElmer (e.g., LANCE® products), Invitrogen (e.g., LanthaScreen® products), and Cisbio Bioassays (e.g., HTRF® products).

In some embodiments, the FRET energy donor and the FRET energy acceptor may be chosen based upon one or more of the fluorophores listed in the table below.

TABLE B

Examples of FRET energy donor and energy acceptor molecules

| FLUOROPHORE | Excitation (nm) | Emission (nm) |
|---|---|---|
| 5-Carboxynapthofluorescein | 512/598 | 563/668 |
| 5-ROX (carboxy-X-rhodamine) | 578 | 604 |
|  | 567 | 591 |
| Alexa Fluor 568 ™ | 577 | 603 |
| Alexa Fluor 594 ™ | 590 | 617 |
|  | 594 | 618 |
| Alexa Fluor 633 ™ | 632 | 650 |
| Alexa Fluor 647 ™ | 647 | 666 |
| Alexa Fluor 660 ™ | 668 | 698 |
| Alexa Fluor 680 ™ | 679 | 702 |
| Allophycocyanin (APC) | 630-645 | 655-665 |
| APC-Cy7 | 625-650 | 755 |
| BOBO ™ -3 | 570 | 602 |
| Bodipy | 492-591 | 509-676 |
| Bodipy TR | 589 | 617 |
| Bodipy TR ATP | 591 | 620 |
| Calcium Crimson ™ | 588 | 611 |
|  | 589 | 615 |
| Carboxy-X-rhodamine (5-ROX) | 576 | 601 |
| Cy3.5 ™ | 581 | 598 |
| Cy5.1 8 | 649 | 666 |
| Cy5.5 ™ | 675 | 695 |
| Cy5 ™ | 649 | 666 |
| Cy7 ™ 710, 743 767, 805 | 710 | 767 |
|  | 743 | 805 |
| Dysprosium | 305-335 | 465-495 |
|  |  | 565-595 |
| Europium | 315-350 | 600-635 |
|  |  | 675-715 |
| Europium (III) chloride | 315-350 | 600-635 |
|  |  | 675-715 |
| FL-645 | 615-625 | 665 |
| Fura Red ™ (high pH) | 572 | 657 |
| LaserPro | 795 | 812 |
| Samarium | 325-355 | 475-505 |
|  |  | 545-575 |
|  |  | 585-615 |
|  |  | 630-660 |

TABLE B-continued

Examples of FRET energy donor and energy acceptor molecules

| FLUOROPHORE | Excitation (nm) | Emission (nm) |
|---|---|---|
| SureLight ® | 640-660 | 660-680 |
| Terbium | 305-335 | 475-505 |
|  |  | 530-560 |
|  |  | 570-600 |
|  |  | 605-635 |
| Texas Red ™ | 595 | 620 |
| Texas Red-X ™ conjugate | 595 | 615 |
| Thiadicarbocyanine (DiSC3) | 651 | 674 |
|  | 653 | 675 |
| Thiazine Red R | 596 | 615 |
| TO-PRO-1 | 515 | 531 |
| TO-PRO-3 | 644 | 657 |
| TO-PRO-5 | 747 | 770 |
| TOTO-3 | 642 | 660 |
| ULight ® | 630-655 | 655-675 |
| Ultralite | 656 | 678 |
| X-Rhodamine | 580 | 605 |
| XRITC | 582 | 601 |
| YO-PRO-3 | 613 | 629 |

The following information may also be considered when selecting a FRET energy donor and FRET energy acceptor combination. U.S. Pat. No. 5,998,146, herein incorporated by reference, describes the use of lanthanide chelate complexes, in particular of europium and terbium complexes combined with fluorophores or quenchers. It also describes properties of the long-lived lanthanide chelate complexes.

FRET systems based on metallic complexes as energy donors and dyes from the class of phycobiliproteins as energy acceptors are known in the art (EP 76 695; Hemmilae, Chemical Analysis 117, John Wiley & Sons, Inc., (1991) 135-139). Established commercial systems (e.g., from Wallac, OY or Cis Bio Packard) use a FRET pair consisting of a lanthanide chelate as the metallic complex and a phycobiliprotein.

The properties of the lanthanide-chelate complexes in particular of europium or terbium complexes are known and can be used in combination with quenchers as well as in combination with fluorophores.

Ruthenium complexes per se are used as fluorophores or luminophores especially for electro-chemoluminescence. Ruthenium-chelate complexes are, for example, known from EP 178 450 and EP 772 616 in which methods for coupling these complexes to biomolecules are also described. Their use as energy donors in FRET systems is not discussed there.

Allophycocyanins have properties such as unusually high extinction coefficients (about 700000 L/M cm) and also extremely high emission coefficients. These are useful prerequisites for their use as fluorophore acceptors in FRET systems. Moreover these dyes are known to be readily soluble in water and stable.

The term low molecular fluorophore refers to fluorophoric dyes having a molecular weight between 300 and 3000 Da. Such low molecular fluorophoric groups such as xanthenes, cyanins, rhodamines and oxazines have considerable disadvantages compared to the APCs with regard to important characteristics. Thus for example their extinction coefficients are substantially lower and are in the range of ca. 100000 L/M cm.

In some embodiments, the methods and assays of the invention make use of homogeneous TR-FRET assay techniques. TR-FRET is a combination of time-resolved fluorescence (TRF) and FRET. TRF reduces background fluorescence by delaying reading the fluorescent signal, for example, by about 10 nano seconds. Following this delay (i.e., the gating period), the longer lasting fluorescence in the sample is measured. Thus, using TR-FRET, interfering background fluorescence, that may for example be due to interfering substances in the sample, is not co-detected, but rather, only the fluorescence generated or suppressed by the energy transfer is measured. The resulting fluorescence of the TR-FRET system is determined by means of appropriate measuring devices. Such time-resolved detection systems use, for example, pulsed laser diodes, light emitting diodes (LEDs) or pulsed dye lasers as the excitation light source. The measurement occurs after an appropriate time delay, i.e., after the interfering background signals have decayed. Devices and methods for determining time-resolved FRET signals are described in the art.

This technique requires that the signal of interest must correspond to a compound with a long fluorescent lifetime. Such long-lived fluorescent compounds are the rare earth lanthanides. For example, Eu3+ has a fluorescent lifetime in the order of milliseconds. TR-FRET requires a FRET energy donor and a FRET energy acceptor, as described above. As with FRET, a TR-FRET energy donor and acceptor pair can be selected based on one or more, including all, of the following: (1) the emission spectrum of the FRET energy donor should overlap with the excitation spectrum of the FRET energy acceptor; (2) The emission spectra of the FRET partners (i.e., the FRET energy donor and the FRET energy acceptor) should show non-overlapping fluorescence; (3) the FRET quantum yield (i.e., the energy transferred from the FRET donor to the FRET acceptor) should be as high as possible (for example, FRET should have about a 1-100%, e.g., a 30%, 40%, 50%, 60%, 70%, 80%, 85%, 90%, 95%, 98%, and 99% efficiency over a measured distance, of 1-20 nm, e.g., 5-10 nm); (4) the FRET signal (i.e., fluorescence) must be distinguishable from fluorescence produced by the sample, e.g., autofluorescence; and (5) the FRET donor and the FRET acceptor should have half lives that allow detection of the FRET signal (e.g., FRET can be bright and can occur on a timescale ranging from 10-9 seconds to 10-4 seconds).

In some embodiments, the TR-FRET donor and the TR-FRET acceptor may be chosen based upon one or more of the fluorophores listed in the table above.

In some embodiments, the TR-FRET donor may be a lanthanide ion, e.g., a lanthanide ion bound to a chelate. In some embodiments, the lanthanide ion may be a europium, terbium, samarium, or dysprosium ion. As used herein, Eu includes Eu and all Eu ions, e.g., Eu3+. In some embodiments, the TR-FRET donor may be DsRed. In some embodiments, the TR-FRET donor may be Ri2. It is to be understood that selection of the appropriate TR-FRET donor requires consideration of the above listed criteria and the specific TR-FRET acceptor selected.

In some embodiments, the TR-FRET acceptor may be selected from the group consisting of fluorescein, Cy5, allophycocyanin (APC—e.g., XL665, d2 (Cisbio), and BG-647), and a fluorescent protein (e.g., GFP, CFP, YFP, BFP, RFP, and other GFP variants).

In some embodiments, the TR-FRET donor may be terbium and the TR-FRET acceptor may be fluorescein. In some embodiments, the TR-FRET donor may be Eu and the TR-FRET acceptor may be Cy5 or APC (e.g., XL665, d2 (Cisbio), BG-647, and Cy5-related TR-FRET acceptors). In one embodiment the FRET energy donor compound is Terbium cryptate and/or the FRET energy acceptor compound is d2.

In some embodiments, the TR-FRET donor and the TR-FRET acceptor may be combined with a second compound that enhances the function of the TR-FRET donor and/or the TR-FRET acceptor. For example, the TR-FRET donor and the TR-FRET acceptor may be combined with cryptate encapsulation to extend the half-life of the fluorophore. Alternatively, or in addition, the TR-FRET donor the TR-FRET acceptor may be combined with, e.g., DELFIA® enhancement system. In some embodiments, the TR-FRET donor and the TR-FRET acceptor may be combined with, for example, buffers, salts, enhancers, chelators, and stabilizers (e.g., photo-stabilizers) that enhance or extend the life or detection of the TR-FRET signal.

Molecules, e.g., proteins, may be labeled directly or indirectly with suitable FRET or TR-FRET donors and acceptors, as described above and described in U.S. Pat. Nos. 4,925,804, 5,637,509, 4,761,481, 4,920,195, 5,032,677, 5,202,423, 5,324,825, 5,457,186, 5,571,897, 7,250,517, US2005/0202565, which are herein incorporated by reference.

Time-resolved FRET is measured in a time-resolved manner by introducing a time delay of approximately 50-150 μs between excitation of the donor and emission measurement of the acceptor. Thus, short-lived background fluorescence generated by the medium, the biological preparation or the direct excitation of the acceptor are not measured and assay sensitivity is increased. A commonly used acceptor molecule is an organic red fluorescent dye called d2 which is 100 times smaller than XL665 with exhibiting photophysical properties very similar to XL665. (Amoravain M, Lyotard S, Jaga D, Lebreton M L, Servent F, Bomer U. Introduction of a new HTRF acceptor, d2: Development of a complete GPCR platform for a Gs, Gi and Gq screening. SBS; 11th Annual Conference; Geneva. 2005.).

Any of a variety of light-emitting and light-detecting instruments can be used to initiate FRET (e.g., excite a FRET donor or excite a reagent capable of exciting the FRET donor) and/or detect an emission produced from said FRET. The light emissions produced by the first and second member of the FRET pair as a result of the above methodologies can be detected or measured visually, photographically, actinometrically, spectrophotometrically, or by any other convenient means to determine the amount thereof, which is related to the amount of each component in the medium.

The binding of the antibody or ligand to the target antigen can be determined qualitatively, i.e. by the presence or absence of the FRET signal; with the absence of any FRET signal being indicative of no binding. Usually the "absence of a FRET signal" is defined by a certain threshold, i.e. after deduction of any background signal. The background signal is usually determined by performing the FRET assay with all reagents but the antibody or ligand to be tested. The binding of the antibody or ligand to the target antigen can be determined quantitavely, i.e. the level or strength of binding can be determined with the FRET method. Towards this end the antibody or ligand to be tested is tested in different concentrations and the half maximal effective concentration (EC50) is determined. EC50 refers to the concentration of the antibody or ligand at which the antibody or ligand binds halfway between the baseline and maximum after a specified exposure time. The EC50 of the dose response curve therefore represents the concentration of the antibody or ligand where 50% of its maximal binding is observed. The KD (dissociation constant) can be calculated from the dose response curve by methods known in the art.

In one embodiment the binding of the antibody or ligand to the target antigen is determined with bioluminescence resonance energy transfer (BRET). Accordingly in one embodiment the energy donor and acceptor compound are a bioluminescence energy transfer (BRET) energy donor and acceptor compound and the energy transfer determined in step iii) is bioluminescence energy transfer (BRET). The BRET assay technology is based on the efficient Resonance Energy Transfer (RET) between a bioluminescent donor moiety and a fluorescent acceptor moiety. BRET is a naturally occurring phenomenon and differs from FRET in that it uses a luciferase as the donor. In one embodiment a luciferase (Rluc) isolated from the sea pansy *Renilla reniformis* and a coelenterazine substrate named DeepBlueC (DBC) are used as the donor. In the presence of oxygen, Rluc catalyzes the transformation of DBC into coelenteramide with concomitant light emission peaking at 395 nm (blue light). When a suitable acceptor is in close proximity, the blue light energy is captured by RET. In one embodiment the acceptor in BRET is a GFP variant (GFP2) that is engineered to maximally absorb the energy emitted by the Rluc/DBC reaction. Excitation of GFP2 by RET results in an emission of green light at 510 nm. Energy transfer efficiencies between Rluc/DBC and GFP2 are determined ratiometrically by dividing the acceptor emission intensity by the donor emission intensity. This ratiometric measurement is referred to as the BRET signal and reflects the proximity of Rluc to GFP. In another embodiment Rluc is used as the donor, the derivative of coelenterazine as its substrate and a yellow fluorescent protein (YFP) as the acceptor.

In one embodiment the binding of the antibody or ligand to the target antigen is determined with an AlphaScreen (Amplified Luminescent Proximity Homogeneous Assay). Accordingly in one embodiment the energy donor and acceptor compound are an alpha screen acceptor and donor bead and the energy transfer determined in step iii) is an energy transfer from a singlet oxygen to an thioxene derivative within the acceptor bead. AlphaScreen is a non-radioactive, homogeneous proximity assay using an "acceptor" and a "donor" bead. AlphaScreen is a bead-based detection system used to study biomolecular interactions in a microplate format. Binding of molecules captured on the beads leads to an energy transfer from one bead to the other, ultimately producing a luminescent/fluorescent signal. Every AlphaScreen assay contains two bead types, donor beads and acceptor beads. Both bead types are coated with a hydrogel which minimizes nonspecific binding and self-aggregation, and provides reactive aldehyde groups for conjugating biomolecules to the bead surface.

Every AlphaScreen assay contains two bead types, donor beads and acceptor beads. Each bead type contains a different combination of chemicals, which are key elements of the AlphaScreen technology. Donor beads contain a photosensitizer, phthalocyanine, which converts ambient oxygen to an excited form of singlet oxygen, upon laser illumination at 680 nm Like other excited molecules, singlet oxygen has a limited lifetime prior to falling back to ground state. Within its 4 sec half-life, singlet oxygen can diffuse approximately 200 nm in solution. If an acceptor bead is within that proximity, an energy transfer from a singlet oxygen to an thioxene derivative within the acceptor bead takes place, subsequently culminating in light production at 520-620 nm. In the absence of an acceptor bead, singlet oxygen falls to ground state and no signal is generated. In one embodiment the cells used in the assay are labelled with biotinilated WGA bound to streptavidin coated donor beads. In one embodiment the acceptor beads are conjugated to Protein A.

The antibody to be tested can easily be labeled with these acceptor beads as Protein A binds to the Fc domain of the antibody.

Methods for labeling the cell surface and the antibody or ligand to be tested or secondary antibody for BRET, FRET or AlphaScreen are known in the art. For example, binding partners can be labeled directly or indirectly (e.g., via a tag like non-peptide tags such as biotin, digoxigenin, fluorescein, dinitrophenol and also peptidic tags such as FLAG, HisTag, cmyc, HA, V5, streptag, ACP/MCP Tag or using avidin-streptavidin interactions), for example as described by Yang et al., Analytical Biochemistry 351:158-160, 2006, which is herein incorporated by reference. ACP-tag and MCP-tag are small protein tags based on the acyl carrier protein. The presence of an added synthase is required for the formation of a covalent link between the ACP-tag or MCP-tag and their substrates, which are derivatives of Coenzyme A. In the labeling reaction, the group conjugated to CoA is covalently attached to the ACP-tag or MCP-tag by a recombinant synthase. Labels can be covalently attached to a tag using either ACP-Synthase (NEB #P9301) for ACP-tag labeling or SFP-Synthase (NEB #P9302) for dual ACP- and MCP-tag labeling.

In one embodiment the target antigen is covalently or noncovalently labelled with the energy donor compound. For example, the protein to be analysed (e.g. the target antigen of the antibody or ligand to be analysed herein) can be labeled by linking it to the 20 kDa DNA repair enzyme human $O^6$-alkylguanine-DNA-alkyltransferase (AGT). This enzyme can build a covalent bond to a $O^6$-benzylguanine (BG) derivative which itself is coupled to the donor or acceptor fluorescent dye. For the generation of cells expressing the labeled target antigen of interest, the cells are transfected with a plasmid encoding the human $O^6$-alkylguanine-DNA-alkyltransferase (AGT) fused to the protein of interest. Following transfection, the fusion protein expressed at the cell surface is labeled using BG-fluorophore and can then be used for FRET based interaction studies. Preferably the target antigen is labeled with the FRET donor molecule.

The antibody or ligand to be analysed (which binds to the labelled target antigen expressed at the cell surface) can be covalently or noncovalently labeled with a energy donor or acceptor compound, e.g. a fluorescent dye or an AlphaScreen bead. It is also possible to label a secondary antibody that binds to the antibody or ligand to be analysed (e.g. anti-human IgG).

Labelling can also be achieved through wheat germ agglutinin (WGA) labelled with a FRET donor or acceptor molecule. Hence in one embodiment the energy donor compound is covalently or noncovalently linked to wheat germ agglutinin (WGA). Thus, instead of transfecting the cells and labeling the fusion proteins as described above, the cells themselves can be labeled with the donor molecule. WGA binds with high affinity to carbohydrates such as N-acetyl glucosamine (GlcNAc) and N-acetylneuraminic acid (also called sialic acid). Due to the omnipresence of such sugar types on the cell surface, binding of WGA conjugated with a donor or acceptor fluorophor allows random labeling of the cell surface. Interaction of an antibody or ligand binding to the antigen of interest embedded in the cell membrane can then be detected by an energy transfer from the WGA-Terbium to the acceptor label coupled directly to the antibody or ligand to be evaluated or to a secondary detection antibody.

In one embodiment the reporter gene is selected from a gene coding for a fluorescent protein or a gene coding for an enzyme whose catalytic activity can be detected. In one embodiment the fluorescent protein is selected from the group consisting of green fluorescent protein (GFP), yellow fluorescent protein (YFP), red fluorescent protein (RFP), Blue fluorescent protein (BFP, Heim et al. 1994, 1996), a cyan fluorescent variant known as CFP (Heim et al. 1996; Tsien 1998); a yellow fluorescent variant known as YFP (Oruro et al. 1996; Wachter et al. 1998); a violet-excitable green fluorescent variant known as Sapphire (Tsien 1998; Zapata-Hommer et al. 2003); and a cyan-excitable green fluorescing variant known as enhanced green fluorescent protein or EGFP (Yang et al. 1996) enhanced green fluorescent protein (EGFP) and can be measured e.g. by live cell imaging (e.g. Incucyte) or fluorescent spectrophotometry. In one embodiment the enzyme whose catalytic activity can be detected is selected from the group consisting of luciferase, beta Galactosidase, Alkaline Phosphatase. In one preferred embodiment the reporter gene is encoding for GFP.

In one embodiment the reporter gene encodes for luciferase. The activity of luciferase can be detected by commercially available assays, e.g. by Luciferase 1000 Assay System (or ONE-Glo™ Luciferase Assay System (both Promega). The Luciferase 1000 Assay System contains coenzyme A (CoA) besides luciferin as a substrate, resulting in a strong light intensity lasting for at least one minute. For assaying the intracellular luciferase, it is necessary to lyse the cells prior to detection. Therefore, a cell lysis buffer was provided separately to the Luciferase 1000 assay system. In comparison, the ONE-Glo™ Luciferase Assay System combines the Luciferase substrate with a cell lysis reagent and also shows a more stable signal. The light which is produced as a by-product of the reaction is collected by the luminometer from the entire visible spectrum. In the examples shown herein the signal was proportional to the amount of produced luciferase and therefore proportional to the strength of the activation of the NFκB promotor. In another embodiment a Luciferase assay is used wherein the luciferase is secreted from the cells. Hence the assay can be performed without lysis of the cells.

The expression of the reporter gene can be directly correlated with the functionality of the ligand or antibody to be tested. For example when using a gene encoding for a fluorescent protein or a gene encoding for luciferase as a reporter gene, the amount of light detected from the cells correlates directly with the target antigen activation or inhibition of the antibody or ligand to be tested.

In one embodiment the antibody or ligand are tested in different concentrations and the half maximal effective concentration (EC50) of reporter gene activation or inhibition is determined. EC50 refers to the concentration of the antibody or ligand at which the antibody or ligand activates or inhibits the reporter gene halfway between the baseline and maximum after a specified exposure time. The EC50 of the dose response curve therefore represents the concentration of the antibody or ligand where 50% of its maximal activating or inhibitory effect on the target antigen is observed.

In one embodiment the cells naturally express the target antigen. In one embodiment the target antigen is a cell surface receptor. In another embodiment the cells are expressing the target antigen after being transfected with a gene copy encoding for said target antigen. In another embodiment cells naturally expressing the target antigen are transfected with an additional gene copy encoding for said target antigen. In one embodiment the cells are transfected with a gene copy encoding for the target antigen fused to a gene copy encoding for the human $O^6$-alkylguanine-DNA-alkyltransferase (AGT). In one embodiment the cells are eukaryotic cells, preferably human or primate cells.

In one embodiment the binding is measured as a dilution curve for determination of KD and EC50 values as outlined above.

The binding of the antibody or ligand to the target antigen elicits a cellular response which results in a modulation of the activity of the response element, either directly or through a cascade of cell signalling. The response element is a DNA element which can be silenced or activated by transcription factors or the like. Response elements are known in the art and are commercially available e.g. in reporter vectors. Usually the response element comprises DNA repeat elements and is a cis-acting enhancer element located upstream of a minimal promotor which drives expression of a reporter gene upon transcription factor binding. Examples for response elements and their transcription factors useful herein are mentioned in the below table:

| Transcription factor/Response element | Description |
|---|---|
| AP1(1) | Monitoring induction of the activator protein 1(AP) and the stress-activated protein kinase/Jun N-terminal kinase (SAPK/JNK) signal transduction pathway. |
| AP1(2) | Monitoring the induction of the protein kinase C (PKC) signal transduction pathway, as well as related pathways such as the MAPK pathway. |
| AP3 | Measuring transcriptional activity of activator protein 3. |
| AR | Measuring transcriptional activity of androgen receptor. The androgen receptor functions as a steroid-hormone activated transcription factor. Upon binding the hormone ligand, the receptor dissociates from accessory proteins, translocates into the nucleus, dimerizes, and then stimulates transcription of androgen responsive genes. |
| CRE(1) | Measuring transcriptional activity of cAMP binding protein (CREB). Several signal transduction pathways are associated with the cAMP response element (CRE), including Jun N-terminal kinase (JNK), p38, and protein kinase A (PKA). Induction of these pathways enables endogenous transcription factors, such as CREB or ATF, to bind CRE. |
| E2F(1) | Measuring transcriptional activity of E2F transcription factor family, including E2F1, E2F2, E2F3, E2F4, E2F5. The E2F protein family plays a crucial role in the control of cell cycle and action of tumor suppressor proteins and is also a target of the transforming proteins of small DNA tumor viruses.These proteins bind preferentially to retinoblastoma protein pRB and mediate both cell proliferation and p53-dependent/independent apoptosis. |
| ELK1 | Measuring transcriptional activity of ELK1. ELK1 is a member of the Ets family of transcription factors and of the ternary complex factor (TCF) subfamily. Proteins of the TCF subfamily form a ternary complex by binding to the serum response factor and the serum reponse element in the promoter of the c-fos proto-oncogene. ELK1is a nuclear target for the ras-raf-MAPK signaling cascade. |
| ER | Measuring the induction of the estrogen response element (ERE). Binding of the activated estrogen receptor to the cis-acting ERE enhancer element induces transcription and activates the luciferase reporter gene. |
| GAS (interferon-gamma activation sequence) | Monitoring the induction of STAT1, a component of JAK/STAT-mediated signal transduction pathways. Cytokines bind and induce receptor dimerization at the cell surface, causing the receptor itself to be phosphorylated. The phosphorylated receptor then acts as a docking site for STAT1. STAT1 is phosphorylated, dimerizes and translocates to the nucleus to regulate transcription. |
| GATA | Measuring transcriptional activity of globin transcription factor (GATA) family. The GATA family of transcription factors contains six zinc-finger binding proteins that regulate differentiation and cell proliferation. GATA family members are involved in hematopoietic, cardiac and gut development. |
| GR | Monitoring the induction of the glucocorticoid response element (GRE) and the glucocorticoid-mediated signaling transduction pathway. |
| HIF-1 | Measuring transcriptional activity of hypoxia inducible factor-1 (HIF-1). HIF-1 binds to the hypoxia-response element and activates genes involved in angiogenesis, glucose metabolis, cell proliferation/survival and invasion/metastasis. |
| HSE | Monitoring the activation of heat shock factor (HSF) and heat shock-mediated signal transduction pathways. |
| IRF-1 | Measuring transcriptional activity of interferon regulatory factor 1. IRF1 is a member of the interferon regulatory transcription factor (IRF) family. IRF1 serves as an activator of interferons alpha and beta transcription, and in mouse it has been shown to be required for double-stranded RNA induction of these genes. |
| ISRE | Monitoring the induction of the STAT1 and STAT2 components of Jak/STAT-mediated signal transduction pathways. Signaling molecules, including type I (IFN-a and -b) and type II (IFN-g) interferons, induce signaling by binding receptors and causing receptor dimerization at the cell surface. This dimerization causes the receptor itself to be phosphorylated and act as a docking site for transcription factors, including STAT1 and STAT2. The STAT proteins are then phosphorylated, dimerize and translocate to the nucleus, where the STAT1 and STAT2 heterodimer regulates transcription by binding to the IFN-stimulated response element (ISRE). |

-continued

| Transcription factor/Response element | Description |
|---|---|
| MEF-1 | Measuring transcriptional activity of myogenic factor 3 (MYOD1). |
| MEF-2 | Measuring transcriptional activity MADS box transcription enhancer factor 2A, 2B, 2C and 2D. |
| MEF-3 | Monitoring the activation of myelin gene expression factor 3. |
| NFAT | Monitoring the induction of nuclear factor of activated T-cells (NFAT)-mediated signal transduction pathways. Several pathways are associated with the NFAT enhancer element, including calcineurin and protein kinase C. |
| NFκB | Monitoring the activation of the nuclear factor of kappa light polypeptide gene enhancer in B-cells (NFκB) signal transduction pathway. NFκB is a transcription regulator that is activated by various intra- and extra-cellular stimuli such as cytokines, oxidant-free radicals, ultraviolet irradiation, and bacterial or viral products. Activated NFκB translocates into the nucleus and stimulates the expression of genes involved in a wide variety of biological functions. |
| p53 | Monitoring p53-mediated signal transduction pathways. p53 is a tumor suppressor that plays a crucial role in a number of cellular processes, including the suppression of cell proliferation after DNA damage. |
| PR | Monitoring the induction of progesterone receptor. |
| RAR | Monitoring the induction of the retinoic acid response element (RARE). |
| RXR | Monitoring the activation of retinoid X receptors (RXR) and RXR-mediated signal transduction pathway. Retinoid X receptors (RXRs) and retinoic acid receptors (RARs) are nuclear receptors that mediate the biological effects of retinoids by their involvement in retinoic acid-mediated gene activation. These receptors exert their action by binding, as homodimers or heterodimers, to specific sequences in the promoters of target genes and regulating their transcription. |
| Smad | Measuring transcriptional activity of a family of Mad-related transcription factors. |
| Sp1 | Measuring transcriptional activity of Sp1. Sp1 is a sequence-specific transcription factor that recognizes 5'-GGGGCGGGGC-3' and closely related sequences, which are often referred to as GC boxes. Sp1 was initially identified as a HeLa cell derived factor that selectively activates in vitro transcription from the SV40 promoter and binds to the multiple GC boxes in the 21-bp repeated elements in SV40. Sp1 has been described as a ubiquitous transcription factor that is required for the constitutive and inducible expression of a variety of genes, such as in cell cycle or mammalian development. |
| SRE | Monitoring the induction of the serum response element (SRE) and the mitogen-activated protein (MAP) kinase signal transduction pathway. |
| SRF | Monitoring the induction of serum response factor (c-fos serum response element-binding transcription factor). |
| Stat1 p84/p91 | Measuring transcriptional activity of signal transducer and activator of transcription 1. Stat1 is a member of the STAT protein family. In response to cytokines and growth factors, STAT family members are phosphorylated by the receptor associated kinases, and then form homo- or heterodimers that translocate to the cell nucleus where they act as transcription activators. This protein can be activated by various ligands including interferon-alpha, interferon-gamma, EGF, PDGF and IL-6. |
| Stat4 | Measuring transcriptional activity of signal transducer and activator of transcription 4. Stat4 protein encoded by this gene is a member of the STAT family of transcription factors. In response to cytokines and growth factors, STAT family members are phosphorylated by the receptor associated kinases, and then form homo- or heterodimers that translocate to the cell nucleus where they act as transcription activators. This protein is essential for mediating responses to IL-12 in lymphocytes, and regulating the differentiation of T helper cells. |
| VDR | Measuring transcriptional activity of vitamin D receptor. VDR is a member of the steroid receptor superfamily. In its ligand bound state, VDR forms heterodimers with RXR and regulates gene expression by binding to specific hormone response elements. The VDR-RXR heterodimer has been shown to bind to VD-responsive elements (VDRE) of osteocalcin and osteopontin genes to stimulate transcription of these genes. |
| YY1 | Measuring transcriptional activity of YY1. YY1 is a ubiquitously distributed transcription factor belonging to the GLI-Kruppel class of zinc finger proteins. The protein is involved in repressing and activating a diverse number of promoters. YY1 may direct histone deacetylases and histone acetyltransferases to a promoter in order to activate or repress the promoter, thus implicating histone modification in the function of YY1. |

In one embodiment said response element of the target antigen is a nuclear response element in the nucleus of the cell. In another embodiment said response element is located on a plasmid in the cell. In one embodiment the assay comprises the preliminary step of transfection of the cells with an expression vector comprising the DNA sequence coding for the reporter gene under the control of the target antigen response element. In one embodiment the target antigen is a cell surface receptor.

In one embodiment the binding to the target antigen and the functionality of the antibody or ligand are measured in the same vial or well. In one embodiment the binding to the target antigen and the functionality of the antibody or ligand are measured in the same testing medium. The advantage of the new assay described herein that no washing steps are required. Preferably the testing medium is a medium that provides conditions for cells to be viable for up to 48 hours. Suitable media are for example Fluorobright or DMEM, as outlined in the examples. In one embodiment the assay is performed in a microtiterplate. In one embodiment the microtiterplate is suitable for high throughput screening. The assay of the present invention can be performed in any format that allows for rapid preparation, processing, and analysis of multiple reactions. This can be, for example, in multi-well assay plates (e.g., 96 wells or 386 wells). Stock solutions for various agents can be made manually or robotically, and all subsequent pipetting, diluting, mixing, distribution, washing, incubating, sample readout, data collection and analysis can be done robotically using commercially available analysis software, robotics, and detection instrumentation capable of detecting FRET, BRET or AlphaScreen signals.

In one embodiment the steps iii) and iv) are performed consecutively or simultaneously.

In one embodiment the FRET is time resolved FRET. In one embodiment the FRET energy donor compound is Terbium cryptate and/or the FRET energy acceptor compound is d2. In one embodiment the target antigen and the response element are part of the NF-κB pathway. In one embodiment the target antigen is selected from a target antigen on Toll-like receptors, TNF receptors, T cell receptor and B cell receptor. Non-limiting examples of antibodies that upon binding to its target result in modulation of the activity of NF-κB are anti-CD40 antibodies, anti-DR5 antibodies, anti-DR4 antibodies, anti-41BB antibodies, anti-Ox40 antibodies and anti-GITR antibodies.

In one embodiment the response element is a NF-κB response element. In one embodiment said response element comprises one or more of the following DNA repeats GGGAATTTCC (SEQ ID NO: 1), GGGGACTTTCC (SEQ ID NO:2), GGGACTTTCC (SEQ ID NO:3), GGGACTTCC (SEQ ID NO:4), ATTGTAGCGTA (SEQ ID NO: 5). In one embodiment said response element comprises 3 to 6, 3 or 6 of the DNA repeats mentioned above. In one embodiment said response element comprises 3 to 6, 3 or 6 of the DNA repeats mentioned above and 1, 2, 3 or 4 additional nucleotides.

In one embodiment said response element comprises a DNA sequence of (SEQ ID NO: 6)
GGGAATTT CCGGGGACTT TCCGGGAATTTCCGGGGACT
TTCCGGGAAT TTCC, (SEQ ID NO: 7)
GGGAATTTCCGGGAATTTCCGGGAATTTCCGGGAATTTCCGGGAATTTCC
GGGAATTTCC, (SEQ ID NO: 8)
GGGACTTCCGGGACTTTCCGGGACTTTCCGGGACTTTCCGGGACTTTCCG
GGACTTTCC, (SEQ ID NO: 9)
GGGACTTTCCATTGTAGCGTAGGGACTTTCCATTGTAGCGTAGGGCTTTC
CATTGTAGCGTAGGGCTTTCC, In one embodiment the binding and/or functionality of the antibody or ligand is compared to the binding and/or functionality of a benchmark antibody or ligand (both measured with the assay as described herein). A benchmark antibody or ligand is a prior art antibody or ligand that binds to the same antigen as the antibody or ligand to be tested and has known properties (e.g. binding and/or functionality).

In one embodiment the assay comprises the preliminary step of transfection of the cells with an expression vector comprising the DNA sequence encoding for the reporter gene under the control of the target antigen response element.

In one embodiment 1000 to 40 000 cells per well are provided in step i). In a preferred embodiment 5000 to 30000 cells or 5000 to 10000 cells per well are provided in step i).

In one embodiment the antibody or ligand is provided in step ii) to achieve a concentration of 120-0.02 nM antibody or ligand per well.

III. Examples

The following are examples of methods and compositions of the invention. It is understood that various other embodiments may be practiced, given the general description provided above.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

For combining functionality and binding assessment, two assays were first optimized and then combined: The luciferase assay which provides information about the functionality of an antibody and an assay which allows studying protein-protein interactions such as the FRET assay. For a combination of both assays, reporter cell lines transfected with the target antigen named "Receptor X" fused to a SNAP tag and labeled with a donor fluorophore are needed. Prior to transfection, the reporter cell lines HeLa NFκB-Luc and HEK NFκB-Luc-GFP were evaluated for their NFκB activation by performing a luciferase assay. Instead of anti-Receptor X antibodies, TNFα was used to test the activation of the NFκB pathway, resulting in an expression of luciferase.

TABLE 1

List of Abbreviations

| Abbreviation | Meaning |
| --- | --- |
| AGT | $O^6$-alkylguanine-DNA alkyltransferase |
| Alpha | Amplified Luminescent Proximity Homogeneous Assay |
| AMP | Adenosine monophosphate |
| APC | Allophycocyanin |
| ATP | Adenosine triphosphate |
| BG | $O^6$-benzylguanin |
| $CO_2$ | Carbon dioxide |

TABLE 1-continued

List of Abbreviations

| Abbreviation | Meaning |
|---|---|
| CoA | Coenzyme A |
| DMEM | Dulbeccos Modified Eagle Medium |
| DMSO | Dimethyl sulfoxide |
| FACS | Fluorescence-activated cell sorting |
| FBS | Fetal bovine serum |
| FRET | Fluorescence Resonance Energy Transfer |
| GFP | Green Fluorescent Protein |
| GlcNAc | N-acetyl glucosamine |
| HEK | Human Embryonic Kidney |
| HeLa | Henrietta Lacks |
| HTRF | Homogeneous Time Resolved Resonance |
| HTS | High Throughput Screening |
| hu | Human |
| IKK | IκB kinase |
| IκB | Inhibitory kappa B protein |
| kDa | Kilodalton |
| Luc | Luciferase |
| Lumi4-Tb | Terbium cryptate |
| minP | Minimal promoter |
| MW | Molecular weight |
| NFκB | Nuclear Factor-kappa B |
| PBS | Phosphate buffered saline |
| PP$_i$ | Pyrophosphate |
| RE | Response element |
| RLU | Relative Luminescence Units |
| RT | Room temperature |
| SPR | Surface Plasmon Resonance |
| TNF | Tumor Necrosis Factor |
| TR | Time Resolved |
| WGA | Wheat Germ Agglutinin |

TABLE 2

Materials

| Material | Tradename | Manufacturer |
|---|---|---|
| Reagents | Lipofectamine ® 2000 | Invitrogen, USA |
| | Lipofectamine ® LTX | Invitrogen, USA |
| | X-tremeGene HP | Roche, Switzerland |
| | Dimethyl sulfoxide | Sigma-Aldrich, USA |
| | Dulbeccos Modified Eagle Medium | Gibco, USA |
| | Fetal bovine serum | Gibco, USA |
| | SNAP-Lumi4-Tb | Cisbio, France |
| | Tag-lite ® reaction buffer 5x | Cisbio, France |
| | Cell Dissociation Buffer | Gibco, USA |
| | WGA-Terbium (0.1 mg/ml) | Cisbio, France |
| | ONE-Glo ™ Reagent | Promega, USA |
| | Luciferin 1000 Reagent | Promega, USA |
| | Opti-MEM ®I Reduced Serum Medium | Gibco, USA |
| | FluoroBrite ™ DMEM | Gibco, USA |
| | Phosphate Buffered Saline | Gibco, USA |
| | GlutaMax-I | Gibco, USA |
| | Hygromycin B | Roche, Switzerland |
| Devices | Tecan Infinite ® M1000 Pro | Tecan, Austria |
| | Vi-cell ™ XR | Beckman Coulter, USA |
| | Viktor³ ™ 1420 Multilabel Counter | PerkinElmer, USA |
| | SpectraMax M5/M5e plate reader | Molecular Devices, USA |
| Antibodies | Antibody-I | Roche, Switzerland |
| | Antibody-II | Roche, Switzerland |
| | Antibody-III | Roche, Switzerland |
| | Antibody-IV | Roche, Switzerland |
| | Antibody-V | Roche, Switzerland |
| | Anti-human-IgG-d2 | Cisbio, France |
| | anti-hu IgG Fcγ-specific goat IgG F(ab)2 | Jackson, USA |

Example 1: Transient Transfection and Labeling of Cells with SNAP-Receptor X Fusion Optimization of the Transient Transfection of HeLa NFκB-Luc Cells The HeLa NFκB-Luc cells had to be transfected with a plasmid carrying the gene encoding for a SNAP-tag® Receptor X fusion. To find out the best transfection method, the cell number seeded per well as well as three different transfection reagents (Lipofectamine® 2000, Lipofectamine® LTX and X-tremeGene HP DNA transfection reagent) were evaluated.

Evaluation of Cell Number

Six different cell numbers were seeded in a 6-well-plate (300 000, 400 000 up to 800 000 viable cells per well) to find the optimal number to be used to achieve 70% confluency after an incubation time of 24 h.

Evaluation of Transfection Reagents

For the evaluation of the transfection reagent, 500 000 viable HeLa NFκB-Luc cells per well were seeded in a 6 well plate and incubated for 24 h at 37° C., 5% CO2. Cells were washed with 1 ml PBS, 2 ml of pre-warmed growth medium added and each well then treated with a different transfection reagent.

The first transfection mix was prepared by mixing 150 μl of Opti-MEM®I Reduced Serum Medium and 10 μl of Lipofectamine® 2000 DNA transfection reagent in a sterile 1.5 ml Eppendorf reaction tube. In a second tube 150 μl Opti-MEM®I Reduced Serum Medium was mixed with 3.5 μg of the SNAP-Receptor X plasmid. After an incubation time of at least 5 minutes at room temperature, the content of both tubes was mixed and incubated for 25 minutes at room temperature.

For the second transfection mix, 1.25 μg of the plasmid was diluted in 500 μl of Opti-MEM®I Reduced Serum Medium. Subsequently, 5 μl of Lipofectamine® LTX was added, mixed gently and incubated for 25 minutes at room temperature.

The third transfection mix was prepared by diluting 2 μg of the plasmid in 200 μl of Opti-MEM®I Reduced Serum Medium. Then, 6 μl of X-tremeGENE HP DNA transfection reagent was added and incubated for 30 minutes at room temperature.

Each transfection mixture was added to the cells in a drop wise manner. The 6-well-plate was gently swirled to ensure even distribution over the entire well. The cells were then incubated for 24 h in a humidified incubator at 37° C. and 5% CO2.

After the incubation, the medium with the transfection mixture was carefully removed and the transfected cells were washed once with 3 ml of PBS. For labeling of the cells with SNAP-Lumi4-Tb, 1.5 ml diluted labeling reagent (100 nM in Tag-lite® buffer) was added to the transfected cells and incubated for 1 h in a humidified incubator. Afterwards, the labeling reagent was removed and the cells were detached by using 500 μl Cell Dissociation Buffer. The detached cells were resuspended in 2.5 ml of PBS, transferred to a 15 ml Falcon tube and washed three times with 5 ml of phosphate buffered saline (PBS) by a 5 min centrifugation step at 300 g. The cell pellet was resuspended in 140 μl Tag-lite® reaction buffer. 100 μl from the cell suspension was used for a 1:5 dilution to determine the cell viability and the viable cell concentration by the Vi-cell™ XR from Beckmann Coulter. To evaluate the protein expression after transfection, the remaining 40 μl of cell suspension were distributed in 2 wells of a white 384-well-plate with flat bottom to measure the terbium signal at a wavelength of 615 nm in a plate reader (Victor3™). In order to compare the level of transfection between the different transfection methods, the terbium signal was normalized to a cell number of 10 000 viable cells per well.

Results

In order to find out the best transfection method, three different transfection reagents were tested in a 6-well-plate: Lipofectamine 2000, Lipofectamine LTX and Xtreme Gene HP. For each reagent, 500 000 viable cells per well were seeded out. The SNAP tag fusion protein was afterwards labeled with the donor fluorophore terbium to perform prospective Tag-lite® experiments. Additionally, the terbium label allows determination of the transfection efficiency when measuring fluorescence at a wavelength of 615 nm. Moreover, the viability of the cells after transfection and labeling was determined (FIG. 1). FIG. 1 shows that Lipofectamine LTX was the best reagent for transfecting HeLa cells. Besides the best viability of the cells after transfection and labeling, also the highest terbium signal could be achieved. In contrast, Xtreme Gene HP as well as Lipofectamine 2000 killed more cells and the level of transfection was lower.

Upscaling of the Transfection from 6-Well Plate to T150 Cell Culture Flasks

After determining the best transfection method a larger number of cells had to be transfected and labeled for the planned experiments for the ongoing project. In addition to HeLa NFκB-Luc cells, also HEK NFκB-Luc-GFP cells had to be transfected. Therefore, 15 Mio viable HeLa NFκB-Luc cells and 11 Mio viable HEK NFκB-Luc-GFP cells were seeded out one day prior to transfection in a T150 cell culture flask in 25 ml of DMEM+10% FBS. The transfection complex for the HeLa cells was prepared by adding 18.75 µg of the SNAP-Receptor X plasmid to 7.5 ml of Opti-MEM®I Reduced Serum Medium, whereas for the HEK cells 37.5 µg of the DNA was diluted in the same volume of transfection medium. After gently mixing the dilution, 75 µl of Lipofectamine® LTX DNA transfection reagent was added. After washing the cells in the T150 cell culture flask, the transfection complex was added drop wise and incubated 24 h in a humidified incubator. Afterwards, the transfected cells were washed again and labeled with 10 ml of a 100 nM labeling reagent dilution by incubation at 37° C. for 1 h in a humidified incubator. The cells were washed three times in PBS and counted using the Beckmann Coulter Vi-cell™ XR. The cells were then centrifuged for 5 minutes at 300 g and resuspended in Tag-lite® reaction buffer to determine the protein expression. Therefore, 10 000 viable cells per well were used in a volume of 20 µl Tag-lite® reaction buffer. The terbium signal was measured in duplicates at a wavelength of 615 nm. The cell suspension was again centrifuged, the supernatant discarded and the pellet resuspended in an appropriate volume of freezing medium which was 90% heat inactivated FBS and 10% DMSO to get 1 Mio cells/ml. Aliquots of 0.5 and 1 ml were frozen at −80° C. in cryovials with a Nalgene® cryogenic vial freezing box containing Isopropanol.

Transient transfection of stable Receptor X expressing cells with Receptor X-SNAP were carried out in the same way as described above but using 4 Mio cells per T75 flasks and 10 µg DNA diluted in 4 ml Opti MEM®I Reduced Serum Medium and 37.5 µl Lipofectamine® LTX. These cells are termed "supertransfected" therein.

Results

Figure 2:
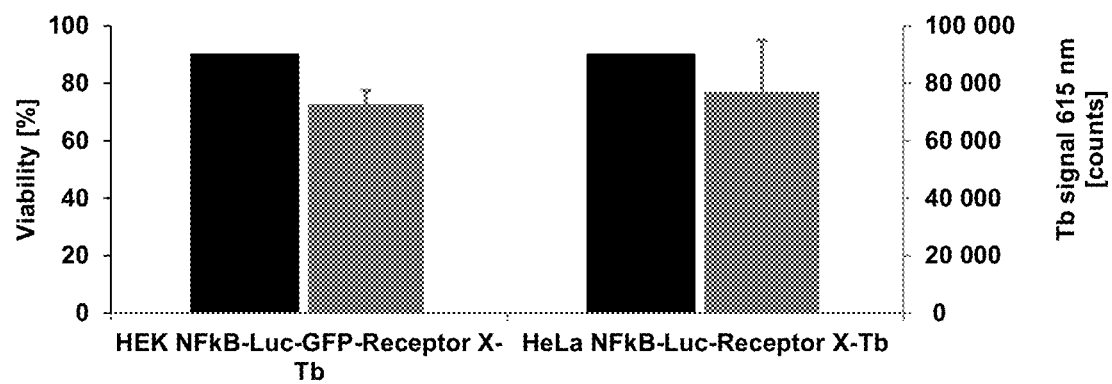
FIG. 2. Determination of the transfection efficiency of Lipofectamine LTX as well as viability measurement of HEK NFκB-Luc-GFP and HeLa NFκB-Luc cells after SNAP-Receptor X transfection and labeling with terbium, a donor fluorescent dye. The terbium signal was measured with 10 000 cells per well at a wavelength of 615 nm.

For the ongoing project, a larger amount of cells was needed. Thus, HEK NFκB-Luc-GFP and HeLa NFκB-Luc cells were transfected in a T150 cell culture flask with Lipofectamine LTX and the terbium signal was determined (FIG. 2).

The terbium signals as well as the viabilities show a similar result for both cell lines. Thus, it was assumed that the expression of SNAP-Receptor X fusion protein on the cells surface was similar and therefore, the results of prospective assays with these cell lines could be compared.

Example 2: Indirect Binding Assay by Tag-Lite®

General Tag-Lite® Protocol

A two-fold dilution series of an anti-human-Receptor X antibody called Antibody-I in Tag-lite® reaction buffer was prepared ranging from 100 nM to 0.2 nM. The anti-human-IgG-d2 detection antibody was diluted in the same buffer to a final concentration of 150 nM per well. HEK NFκB-Luc-GFP cells transiently transfected with the SNAP-Receptor X plasmid and labeled with terbium were used in each assay. The cell line was thawed and washed with 10 ml of PBS by centrifugation for 5 minutes at 350 g. The supernatant was discarded and the pellet was resuspended in Tag-lite® reaction buffer to obtain 1 Mio cells/ml. In a Tag-lite® assay, the cells are not used at a certain cell number, but instead they are adjusted to a certain Tb signal. To find out how many cells have to be used per well in the assay, 10 µl of the resuspended cells (10000 cells per well) were mixed with 10 µl of Tag-lite® reaction buffer in a 384-well-plate in triplicates and the terbium signal at 615 nm determined in a Victor3™ plate reader. For the Tag-lite® assay the cell number was then adjusted to obtain a terbium signal between 20 000 and 30 000 counts per well determined by the Victor3™ plate reader. The Tag-lite® assay was pipetted using 10 µl of the diluted cells, 5 µl of anti-human-IgG-d2 and 5 µl of the dilution series of the antibody. As a blank, 10 µl of the cells, 5 µl of the secondary antibody and 5 µl of buffer was pipetted. All measurements were done in triplicates. The plate was measured after 0 h, 2 h and 4 h of incubation at room temperature with the Tecan Infinite® M1000 Pro plate reader.

All following Tag-lite® experiments including the comparison of different anti-Receptor X IgGs and constructs, evaluation of various detection antibody concentrations, incubation temperature and the influence of incubation media were pipetted using this protocol. Exceptions or changes from the general protocol are stated in the result section.

Results

Figure 3:
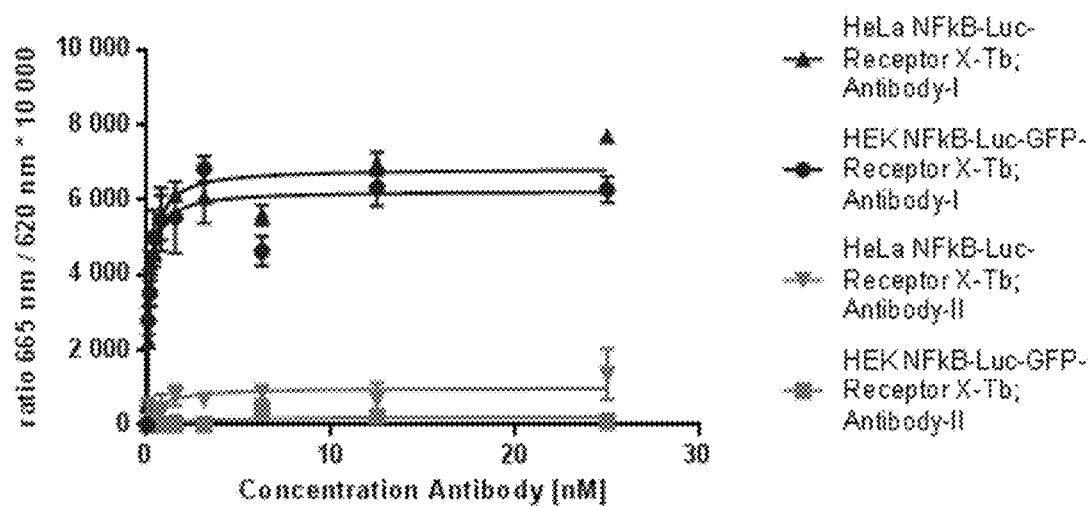
FIG. 3. Tag-lite® indirect binding assay with Antibody-I and Antibody-II to Receptor X expressing HEK NFκB-Luc-GFP and HeLa NFκB-Luc cells. The antibodies were diluted ranging from 25 nM to 0.05 nM in a two-fold dilution series. A concentration of 150 nM for the d2-labeled secondary antibody was used. The binding curve was fitted by nonlinear regression with Graph Pad Prism 6.0.

After transfection and labeling, both cell lines were tested in an indirect Tag-lite® binding assay with two different IgGs (Antibody-I and -II) targeting Receptor X (FIG. 3). FIG. 3 shows that Antibody-I binds better to both cell lines (Receptor X expressing HEK NFκB-Luc-GFP and HeLa NFκB-Luc cells) than Antibody-II. The binding signal of Antibody-I was for both cell lines of the same strength. For Antibody-II only a weak signal can be detected for the HeLa NFκB-Luc-Receptor X-Tb cells and no binding can be seen at HEK NFκB-Luc-GFP-Receptor X-Tb cells. Thus, Antibody-I was used for the ongoing experiments.

Figure 4:
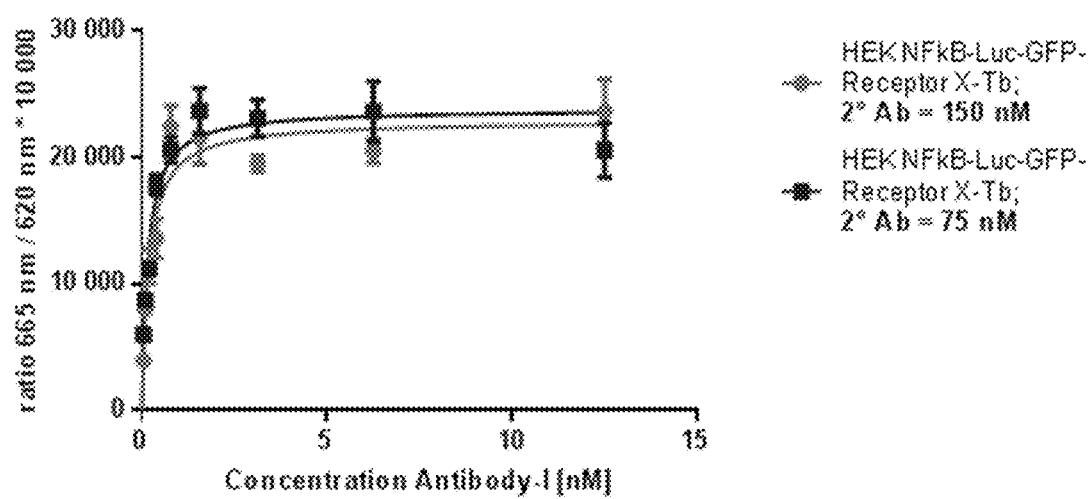
FIG. 4. Indirect Tag-lite® binding assay with Antibody-I binding to Receptor X expressing HEK NFκB-Luc-GFP cells. Antibody-I was diluted from 12.5 nM to 0.025 nM in a two-fold dilution series. The d2-labeled secondary antibody was used in a concentration of 150 nM or 75 nM. The binding curve was fitted by nonlinear regression with Graph Pad Prism 6.0.

The d2 labeled anti-human-IgG which was used as secondary antibody should be at least in a threefold molar excess compared to the primary antibody. Instead of using a concentration of 150 nM as in the previous assays, 75 nM final per well were tested and the results compared (FIG. 4). FIG. 4 shows that there was no significant difference between concentrations of 150 or 75 nM of secondary antibody. For the binding curve with 150 nM, a KD value of 0.19 nM±0.05 nM (R2=0.93) was determined, whereas for the concentration of 75 nM a KD of 0.16 nM±0.03 nM (R2=0.95) was found. Thus, if using the primary antibody in concentrations up to 20 nM, 75 nM for the secondary antibody was used in all ongoing experiments.

Figure 5:
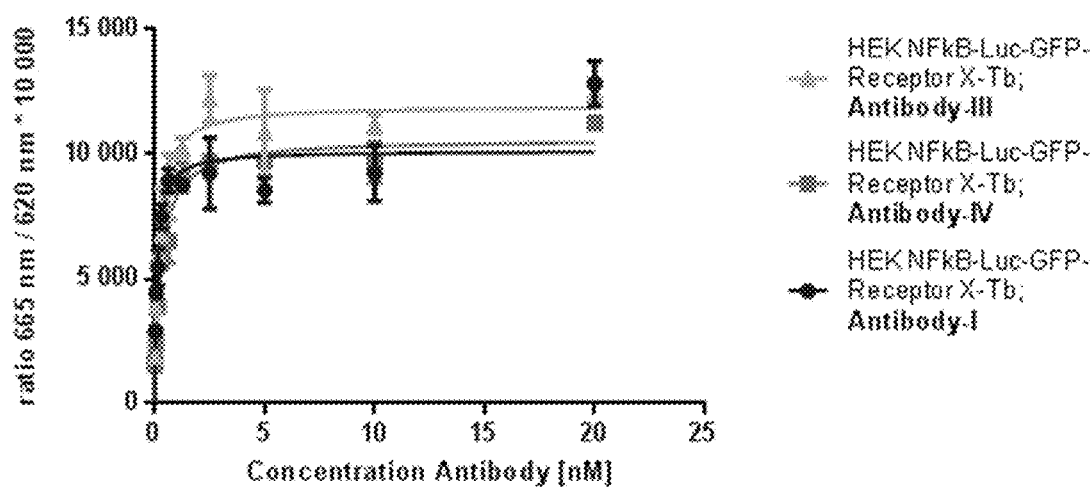
FIG. 5. Indirect Tag-lite® binding assay with Antibody-I, Antibody-III and Antibody-IV to Receptor X expressing HEK NFκB-Luc-GFP cells. All antibodies were diluted from 20 nM to 0.04 nM in a two-fold dilution series. The d2-labeled secondary antibody was used at a concentration of 75 nM. The binding curve was fitted by nonlinear regression with Graph Pad Prism 6.0.

Instead of using Antibody-I which is an IgG, also two different Receptor X antibody constructs were tested for their binding, namely Antibody-III and -IV (FIG. 5).

All antibodies and antibody like constructs show similar binding and KD values with 0.11 nM±0.03 nM (R2=0.85) for Antibody I, 0.18 nM±0.02 nM (R2=0.97) for Antibody-III and 0.28 nM±0.04 nM (R2=0.98) for Antibody-IV.

Figure 6:
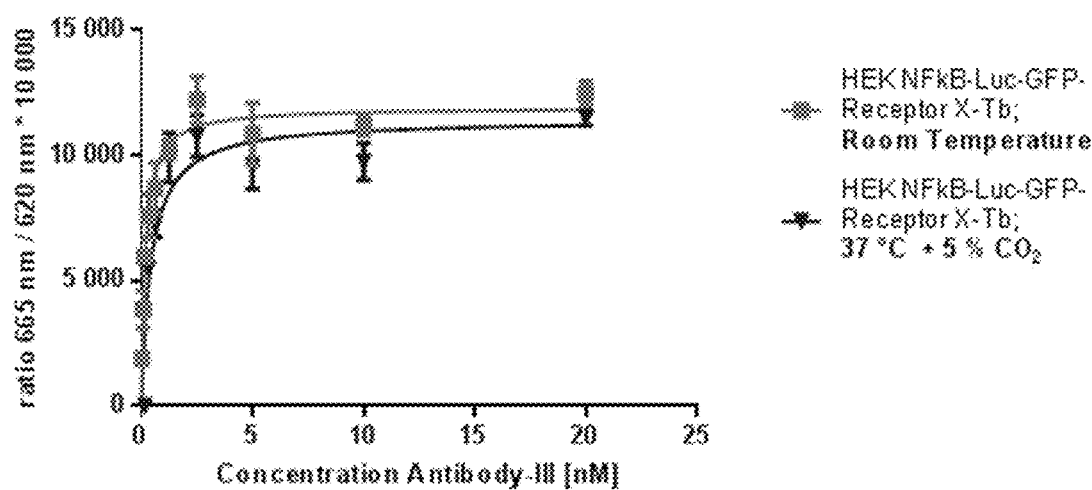
FIG. 6. Indirect Tag-lite® binding assay of Antibody-III to Receptor X expressing HEK NFκB-Luc-GFP cells. The antibody was diluted at a concentration ranging from 20 nM to 0.04 nM in a two-fold dilution series. The d2-labeled secondary antibody was used in a concentration of 75 nM. Incubation at room temperature was compared to incubation at 37° C. The binding curve was fitted by nonlinear regression with Graph Pad Prism 6.0.

For the combination of a luciferase assay with the Tag-lite® binding assay it might be necessary to incubate the cells at 37° C. rather than room temperature (RT) which is commonly used for the binding assay. Therefore, binding at 37° C. had to be assessed (FIG. 6). The KD value determined for the incubation at RT was with 0.18 nM±0.02 nM (R2=0.97) only slightly lower than for the incubation at 37° C., (KD was 0.43 nM±0.18 nM (R2=0.85)). However, binding for both was in the low nanomolar range and therefore comparably strong.

Figure 7:
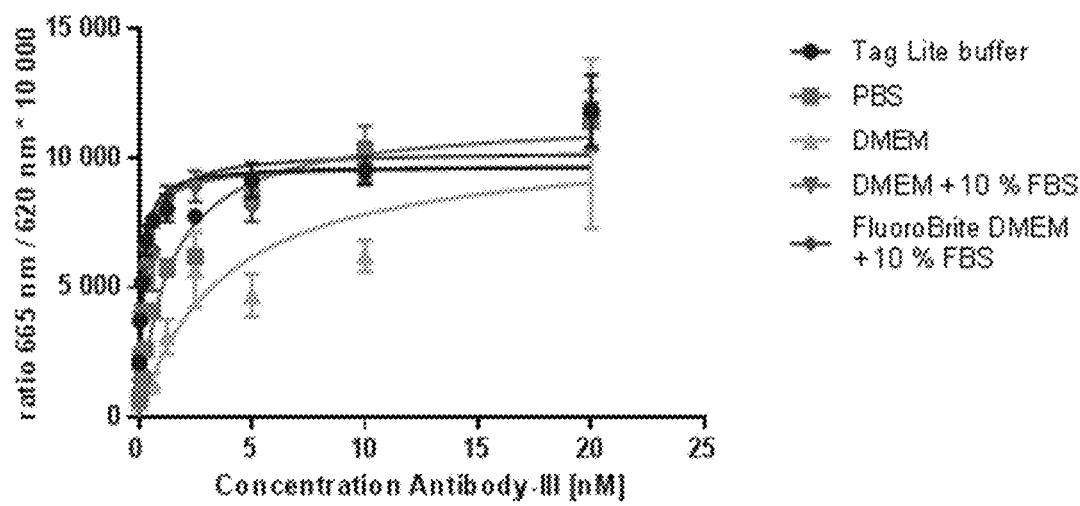
FIG. 7. Indirect Tag-lite® binding assay of Antibody-III binding to Receptor X expressing HEK NFκB-Luc-GFP cells. The antibody was diluted at a concentration ranging from 20 nM to 0.04 nM in a two-fold dilution series. The d2-labeled secondary antibody was used at a concentration of 75 nM. Different buffers and media for the dilutions were compared. The binding curve was fitted by nonlinear regression in Graph Pad Prism 6.0.

Instead of using Tag-lite® buffer or PBS for the binding assay, other media were tested which might be more suitable for the luciferase assay (FIG. 7). FIG. 7 shows that PBS and DMEM decreased the binding of the antibody construct to the receptor. DMEM/10% FBS or FluoroBrite DMEM/10% FBS showed similar results compared to the generally used Tag-lite® buffer and are therefore suitable alternatives for the combination assay.

Time Dependent Stability of the Receptor X on Transiently Transfected Cells after Thawing After transient transfection of the HEK NFκB-Luc-GFP cells with the SNAP-Receptor X plasmid, the cells were frozen and used for the daily experiments. To determine the stability of the receptors after taking thawed transiently transfected cells in culture, an indirect Tag-lite® binding assay was performed every day for three days. Therefore, thawed cells were splitted into 4 wells of a 6-well-plate and cultured in 4 ml FluoroBrite™ DMEM+10% FBS. Every day, the cells of one well of the 6-well-plate were detached, 5 minutes centrifuged at 350 g and resuspended in Fluoro-Brite™ DMEM+10% FBS to a final concentration of 1 Mio cells/ml. 10 000 cells per well were mixed then with a two-fold dilution series of Antibody-III in FluoroBrite™ DMEM+10% FBS medium ranging from 80 nM to 0.16 nM to test the binding. The anti-human-IgG-d2 detection antibody was diluted in the same medium to a concentration of 75 nM final per well. The terbium signal was monitored daily.

Results

Figure 8:
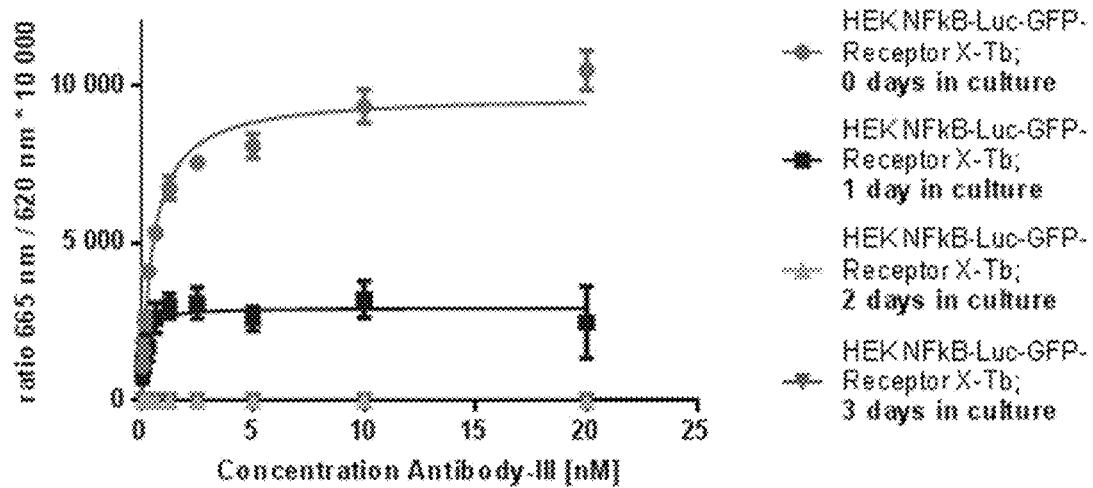
FIG. 8. Indirect Tag-lite® binding assay of Antibody-III binding to Receptor X expressing HEK NFκB-Luc-GFP cells. The experiment was performed directly after thawing the cells and every following day for 3. The antibody was diluted ranging from 20 nM to 0.04 nM in a two-fold dilution series. The d2-labeled secondary antibody was used at a concentration of 75 nM. The binding curve was fitted by nonlinear regression with Graph Pad Prism 6.0.

The presence of the receptor on the cell surface of the transiently transfected cells was monitored over time. Directly after thawing the cells (day 0) and also the following 3 days, an indirect Tag-lite® binding assay (FIG. 8) as well as a measurement of the terbium signal of the cells (FIG. 9) was performed by using 10 000 thawed or cultured cells per well. FIG. 8 shows that the binding signal significantly decreased from day 0 to day 1 and was completely absent at day 2 and 3. The ratio of 665 to 620 nm*10 000 was for time point day 0 was approximately 10 000, whereas 1 day later, Bmax was approximately 3000, which represents 70% of the original signal. The KD value for time point day 0 and day 1 were both in the nanomolar range with 0.49 nM±0.08 nM (R2=0.98), and 0.12 nM±0.03 nM (R2=0.87) respectively.

Figure 9:
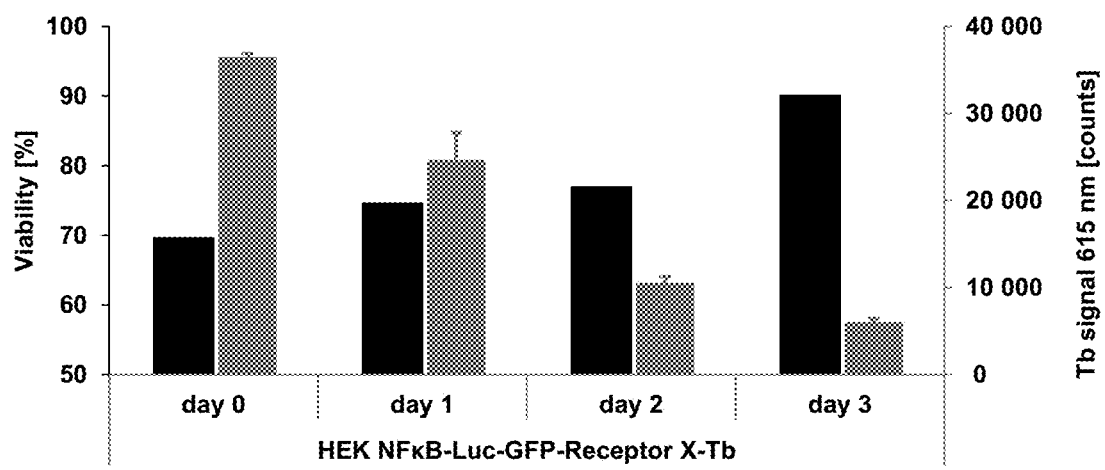
FIG. 9. Determination of the terbium signal and viability of labeled Receptor X expressing HEK NFκB-Luc-GFP cells. The terbium signal was measured directly after thawing and each following day until day 3. 10 000 cells per well were seeded every day and measured at a wavelength of 615 nm.

FIG. 9 is in line with the results depicted in FIG. 8 showing a decrease in terbium signal over time. In contrast, the viability increased from day to day.

After in depth evaluation of the parameters for the Tag-lite® assay also the conditions for the luciferase assay had to be optimized.

Evaluation of the HTRF Raw Data

For the analysis of the assays, the raw data were first edited by Microsoft Excel. In a HTRF assay variations in the results can occur from well to well due to the pipetting steps of the cells, medium additives and from the number of lysed cells per well. To minimize those variations, the emission of the acceptor was normalized to the emission of the donor signal in each well by calculating the ratio of 665 nm to 620 nm:

"ratio=" "665 nm"/"620 nm" "*10000".

The calculated ratio values were evaluated by the software called GraphPad Prism 6.0. The binding curves were fitted with nonlinear regression. Bmax and KD were determined using the "One site—specific binding" model using the equation:

$$Y = (B_{max} \cdot X)/(K_D + X).$$

Example 3: Luciferase Assay

Evaluation of the Luciferase Activation of Two Different Cell Lines

HeLa NFκB-Luc cells used for transient transfection as well as already stably transfected NFκB-Luc-Receptor X cells were compared for their luciferase activity upon stimulation with TNFα

The method used was the Luciferase 1000 assay system (Promega). Therefore, both cell lines were seeded in a white 96-well-plate with a cell number of 20 000 cells per well in 100 μl growth medium (DMEM+10% FBS+1% GlutaMax-I+200 μg/ml Hygromycin B) the day before activation. In addition, the same cells were also seeded in 3 wells of a transparent 96-well-plate to determine the confluency, attachment and contamination status microscopically before activation. After 24 h of incubation at 37° C., 5% CO2, a two-fold dilution series of TNFα was prepared ranging from 25 ng/ml to 0.8 ng/ml. 100 μl of each dilution was added to the cells in triplicates followed by an incubation step for 6 h at 37° C. and 5% CO2. Afterwards, the cells were washed three times with 200 μl PBS per well by a 5 minute centrifugation step at 350 g. For detection of the produced luciferase, the cells had to be lysed. Therefore, 40 μl of lysis buffer was added to each well and incubated for 2 hours at −80° C. to ensure lysis. After adjusting the cells to room temperature, 100 μl of Luciferase 1000 assay reagent was added to each well in the dark and light emission at all wavelengths of the entire visible spectrum was measured immediately by the SpectraMax M5/M5e plate reader with 500 ms integration time. As a blank, the signal of the lysed cells with the luciferase reagent was subtracted.

The light which was produced as a by-product of the reaction was collected by the luminometer from the entire visible spectrum.

The same protocol was also used for the comparison of the Hela NFκB-Luc cells with the HEK NFκB-Luc-GFP cell line.

Different Activation Methods in Comparison

The same assay as described above was performed in triplicates, but only with transiently transfected HEK NFκB-Luc-GFP-SNAP-Receptor X cells seeded at 80 000 cells per well in DMEM+10% FBS. Besides the activation through TNFα receptors, Antibody-I was used to bind to Receptor X which should also be able to activate the NFκB pathway upon oligomerisation. Therefore, a four-fold dilution series of Antibody-I ranging from 120 to 0.03 nM was prepared and 50 μl of each concentration added to the cells followed by an incubation step for 15 minutes at 37° C. and 5% CO2. For hypercrosslinking of the receptor which is required to activate the NFκB pathway, 50 μl of a secondary antibody (anti-hu IgG Fcγ-specific goat IgG F(ab)2) was used. The concentration of this secondary antibody was kept constant at 480 nM which translates into an at least four-fold molar excess compared to the primary antibody.

Comparison of the Luciferase 1000 and the ONE-Glo™ Luciferase Assay System

Besides the Luciferase 1000 assay system, also the ONE-Glo™ Luciferase assay system was tested and the results compared. Therefore, transiently transfected HEK NFκB-Luc-GFP-SNAP-Receptor X cells were tested in comparison to stably transfected HEK NFκB-Luc-GFP-Receptor X cells which served as a positive control. Additionally, the activation by TNFα as well as by Receptor X was analyzed.

Both cell lines were seeded in two white 96-well-plates (one plate for each assay system) with a cell number of 30 000 cells per well in 150 μl DMEM+10% FBS the day before activation. In addition, the same cells were also seeded in 3 wells of a transparent 96-well-plate to determine the confluency, attachment and contamination status microscopically before activation. After 24 h incubation at 37° C. and 5% CO2, 10 nM of the primary Antibody-III was added to the wells tested for the Receptor X activation. After another 15 minutes of incubation, 40 nM of the secondary antibody or 50 ng/ml TNFα was added. The plates were incubated for 48 h at 37° C. and 5% CO2.

One plate was treated as described above for the Luciferase 1000 assay system. Briefly, the cells were washed, lysed, frozen, thawed and measured after adding the luciferase reagent. As a blank, the signal of the lysed cells without activation was subtracted. The other plate was used for the ONE-Glo™ Luciferase assay system. Therefore, an appropriate volume of the supernatant of each well was removed to have a final volume of 100 μl per well. 100 μl of ONE-Glo™ Luciferase reagent was added per well. After 5 minutes of incubation in the dark, light emission was measured by the SpectraMax M5/M5e plate reader with 500 ms integration time. As a blank, the signal of the lysed non-activated cells with the luciferase reagent was subtracted. The measurement was done in triplicates.

Results

HeLa NFκB-Luc cells were first compared in a luciferase assay with HeLa NFκB Luc-Receptor X cells. The latter are known for their ability to activate the NFκB pathway by TNFα receptors, thus they were used as a positive control (data not shown). Almost the same luminescence signal was reached by the HeLa NFκB-Luc cells as by the positive control. Thus, the NFκB pathway could be activated well by TNFα meaning that the cells could be used for transfection of the plasmid with the genes encoding for SNAP-Receptor X.

HEK NFκB-Luc-GFP cells were tested and compared to HeLa NFκB-Luc cells (data not shown). This cell line would preferably be used to develop the combinatory assay due to its second reporter gene which enables an additional tool for detecting gene expression.

HEK NFκB-Luc-GFP cells showed a higher signal than HeLa NFκB-Luc cells. As both cell lines can be used for a luciferase assay, each of them was transfected with the SNAP-Receptor X plasmid.

Figure 10:
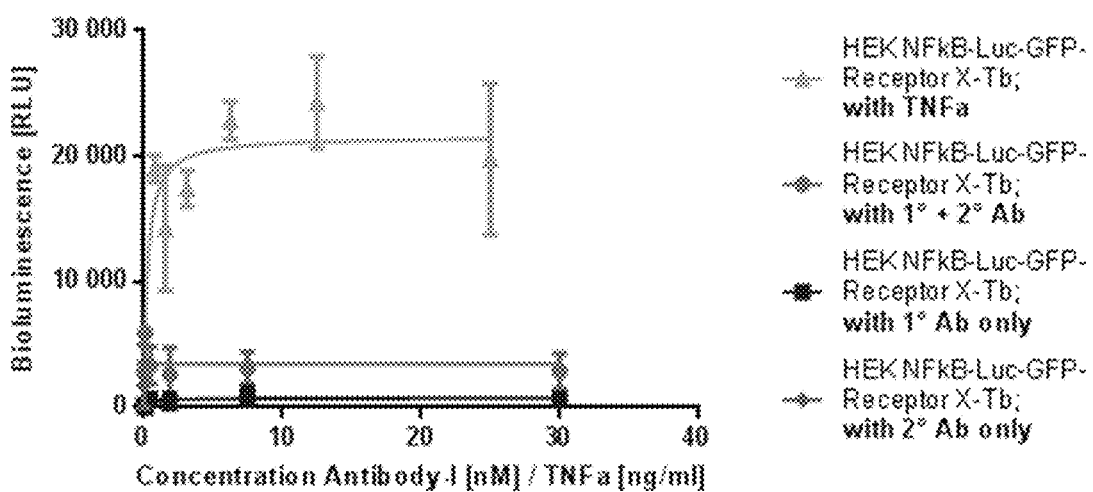
FIG. 10. Luciferase 1000 assay system using Antibody-I and TNFα to Receptor X expressing HEK NFκB-Luc-GFP cells after 6 h of incubation. The dilution series of TNFα (two-fold) ranged from 25 to 0.8 ng/ml, the one of Antibody-I (four-fold) ranged from 30 to 0.03 nM. Antibody-I and the secondary antibody alone were used as controls. The binding curve was fitted by nonlinear regression with Graph Pad Prism 6.0.

After transfection and labeling of the HEK NFκB-Luc-GFP cells with Receptor X-SNAP, Antibody-I was used for the initial luciferase assay and compared to the activation by TNFα. Antibody-I as the primary antibody as well as the secondary antibody were used alone as negative controls (FIG. 10). FIG. 10 shows a strong activation of the NFκB pathway by TNFα. Antibody-I and the secondary antibody alone were not able to activate the pathway. There was only a very weak luminescence signal detected for the combination of both antibodies. In conclusion, Antibody-I was determined to be the best binder, but did not show good functionality in this setting.

Figure 11:
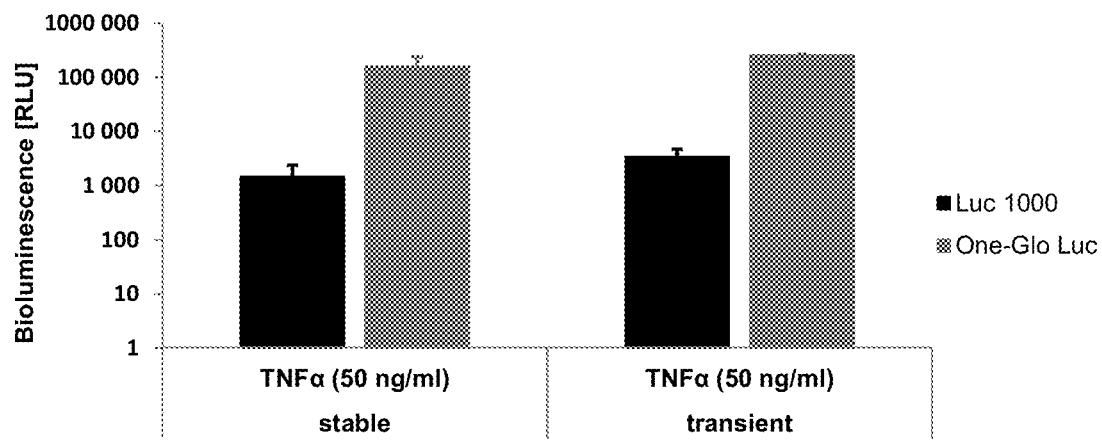
FIG. 11. ONE-Glo™ Luciferase assay system compared to Luciferase 1000 assay system after 48 h of incubation upon activation by TNF-α. The NFκB pathway of stably transfected HEK NFκB-Luc-GFP-Receptor X cells and transiently transfected HEK NFκB-Luc-GFP-Receptor X-Tb cells was activated through TNFα (50 ng/ml).

Furthermore, two different luciferase assay systems were evaluated, the ONE-Glo™ and the Luciferase 1000 system (FIG. 11). Therefore, TNFα was used for activation of the NFκB pathway of stably and transiently transfected Receptor X expressing HEK NFκB-Luc-GFP cells. Instead of a 6 h incubation time after activation, 48 h were used to give the cells more time for expressing luciferase. FIG. 11 shows that the ONE-Glo™ Luciferase assay system was more sensitive to the light released by the luciferase catalyzed reaction from luciferin to oxyluciferin. Due to the higher luminescence signal as well as the faster and easier to perform assay procedure, the ONE-Glo™ Luciferase assay system was used for the ongoing experiments.

Figure 12:
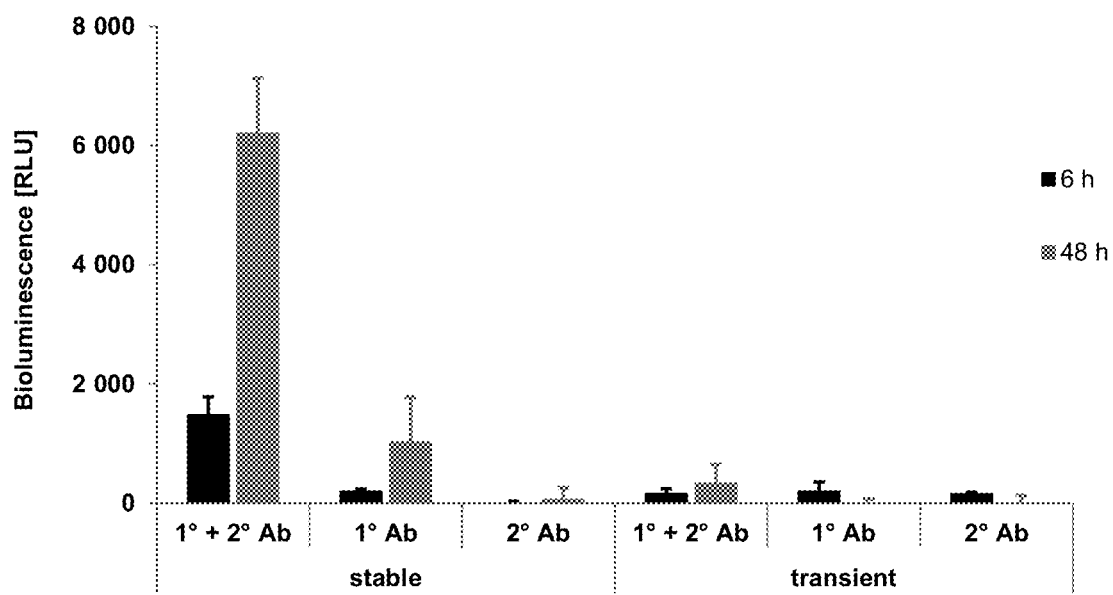
FIG. 12. ONE-Glo™ Luciferase assay system after 6 h and 48 h of incubation. The NFκB pathway of stably transfected HEK NFκB-Luc-GFP-Receptor X cells and transiently transfected HEK NFκB-Luc-GFP-Receptor X-Tb cells was activated by Antibody-III (10 nM) as a primary antibody and anti-hu IgG Fcγ-specific goat IgG F(ab)2 as a secondary antibody (40 nM).

In the following experiment the incubation times of 6 h and 48 h were compared by using the same cells as in the previous experiment. Antibody-III as the primary antibody was used at a concentration of 10 nM and the secondary antibody (anti-hu IgG Fcγ-specific goat IgG F(ab)2) was used at a concentration of 40 nM (FIG. 12).

The stably transfected HEK NFκB-Luc-GFP-Receptor X cells clearly indicated that after 48 h of incubation, more luciferase was produced by the cells, resulting in a stronger bioluminescent signal. Antibody-III alone activated to a lower extent the pathway which was expected as it can already trimerise the receptor. The signals of the transiently transfected cells were significantly lower. Especially for the 6 h incubation there was no major difference in bioluminescence between the combination of both antibodies and each antibody on its own whereas there was a slight difference for the 48 h value.

"Down-Scaling" from 96- to 384-Well-Plates

For the combination assay of functionality and binding, it was necessary to transfer the luciferase assay which is usually done in a 96-well-plate to a 384-well-plate. The ONE-Glo™ Luciferase assay was performed for a 96-well-plate, but instead of using 30 000 cells per well, only 5000 cells were used. The primary and secondary antibodies were kept at a constant concentration of 10 nM and 40 nM, respectively, whereas TNFα was used at a concentration of 50 ng/ml. After 24 h of incubation at 37° C. and 5% CO2, an appropriate volume of the supernatant was removed to have a volume of 15 μl remaining in each well. 15 μl of ONE-Glo™ Luciferase reagent was added per well. The measurement was done with stable HEK NFκB-Luc-GFP-Receptor X cells in triplicates.

Additionally two different cell numbers (5 000 and 10 000 cells per well) were evaluated using the same protocol as described above.

Results

Combining functionality and binding assessment was thought to be used for High-Throughput-Screenings (HTS).

Figure 13:
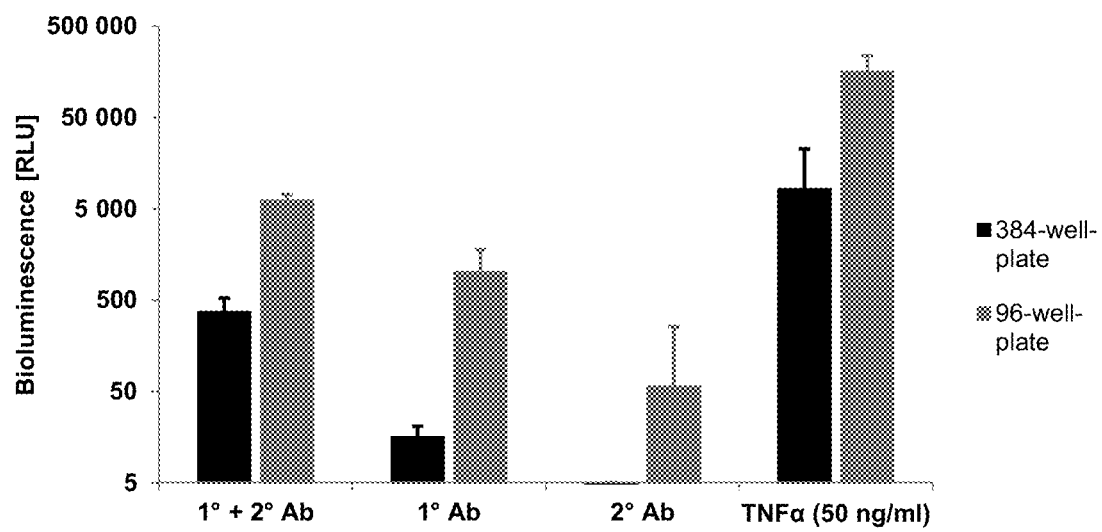
FIG. 13. ONE-Glo™ Luciferase assay system performed in a 96-well-plate as well as in a 384-well-plate after 24 h of incubation. The NFκB pathway of stably transfected HEK NFκB-Luc-GFP-Receptor X cells was activated through Antibody-III (10 nM) as a primary antibody and anti-hu IgG Fcγ-specific goat IgG F(ab)2 as a secondary antibody (40 nM).

For this reason and also for the reason of costs and to bring the luciferase assay in line with Tag-lite® experiments, down-scaling from a 96-well-plate to 384 wells was tested (FIG. 13).

In overall, FIG. 13 shows a slightly stronger signal for the 96 than for the 384-well-plate. Nevertheless, even though the signal was lower in 384 wells than in 96 wells, the result regarding the activation or functionality remains the same. Thus, the ongoing luciferase assays were performed in 384-well-plates.

Figure 14:
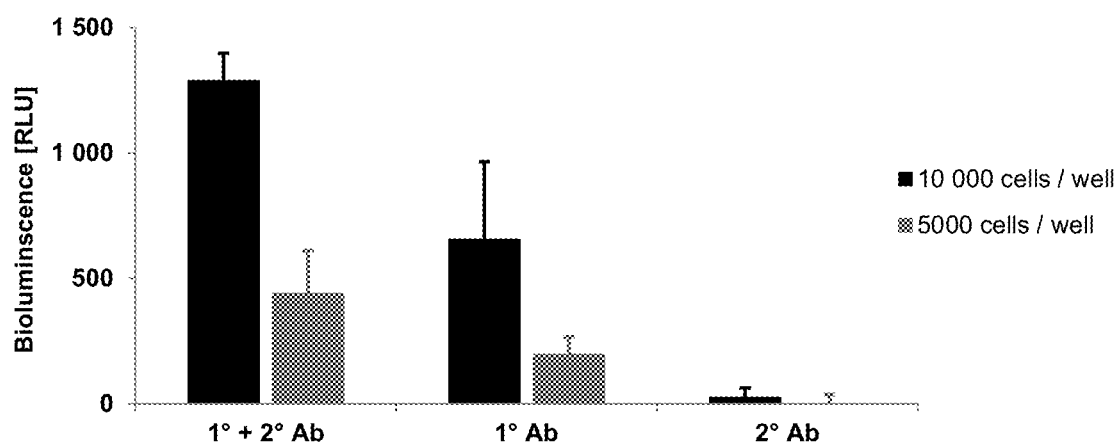
FIG. 14. ONE-Glo™ Luciferase assay system performed in a 384-well-plate after 6 h of incubation. The NFκB pathway of stably transfected HEK NFκB-Luc-GFP-Receptor X cells was activated through Antibody-III (10 nM) as a primary antibody and anti-hu IgG Fcγ-specific goat IgG F(ab)2 as a secondary antibody (40 nM).

For the down-scaling of the luciferase assay, a cell number of 5 000 viable cells per well was calculated, but for the binding experiments sometimes 10 000 cells are needed per well to have a high enough fluorescent signal of the donor fluorophore for the FRET signal. The feasibility of using either 5 000 or 10 000 was tested with the ONE-Glo™ Luciferase assay system using stably transfected HEK NFκB-Luc-GFP-Receptor X cells (FIG. 14). FIG. 14 shows that there was even a stronger signal for the bioluminescence when using 10 000 viable cells per well. Despite keeping the other parameters—such as the amount of added antibodies—constant, more luciferase could be produced by the cells resulting in a stronger bioluminescent signal.

Now, all the parameters for a combination of a binding and a luciferase assay were aligned. Unfortunately, neither of the cell line was suitable for a combination assay. There were stably transfected HEK NFκB-Luc-GFP-Receptor X cells available, which show good results in a functionality assay, but cannot be used for a normal Tag-lite® assay due to the lack of the donor fluorophore and there were transiently transfected HEK NFκB-Luc-GFP-Receptor X-Tb cells available, which show good results in the binding assay, but cannot be activated very well. Therefore, two approaches were tested. On one hand a WGA based FRET assay on stably transfected cells and on the other hand a supertransfection of the stably transfected cells with the Receptor X-SNAP construct.

Optimization of the Concentration of the Primary Antibody

All the luciferase assays were performed using 10 nM of the primary antibody and 40 nM of the secondary. The aim of this assay was to titrate the first antibody with five dilutions and to keep the secondary antibody in a 1:4 ratio for detection.

The ONE-Glo™ Luciferase assay was performed using transiently transfected HEK NFκB-Luc-GFP SNAP-Receptor X cells, stably transfected HEK NFκB-Luc-GFP-Receptor X cells as well as the transiently supertransfected cells. For all three cell lines 5 000 cells per well were seeded out in a 384-well-plate in 15 µl DMEM+10% FBS and incubated for at least 12 h at 37° C. and 5% CO2 before activation. A two-fold dilution series of the primary Antibody-III was prepared and added to the wells ranging from 40 nM to 2.5 nM per well. After 15 minutes of incubation, the secondary antibody (anti-hu IgG Fcγ-specific goat IgG F(ab)2) was added to the wells at concentrations ranging from 160 nM to 10 nM per well, to keep the secondary antibody in a fourfold molar excess compared to the primary antibody. The plates were incubated at 37° C. and 5% CO2. After 24 h of incubation, an appropriate volume of the supernatant was removed to have a final volume of 15 µl per well remaining. 15 µl of ONE-Glo™ Luciferase reagent was added per well. After 5 minutes of incubation in the dark, light emission was measured by the SpectraMax M5/M5e plate reader with 500 ms integration time. As a blank, the signal of the lysed non-activated cells with the luciferase reagent was subtracted. The measurement was done in triplicates.

Ratio Optimization of the Cross-Linking Antibody

For the functionality assay, the secondary antibody (anti-hu IgG Fcγ-specific goat IgG F(ab)2) was used for cross-linking. To combine the luciferase assay with the binding assay, an antibody was necessary which is labeled with the acceptor fluorophore d2. Either the anti-hu IgG Fcγ-specific goat IgG F(ab)2 had to be labeled or the anti-human-IgG-d2 from CisBio could be used. The primary antibody was kept at a constant concentration of 40 nM, which was optimized in the assay before, whereas the ratio of primary antibody to secondary antibody changed from 1:1 to 1:5 ratio.

Example 4: Indirect WGA-HTRF

The anti-human-IgG-d2 detection antibody was diluted in Tag-lite® reaction buffer to a concentration of 75 nM final per well. A two-fold dilution series of Antibody-III in Tag-lite® reaction buffer was prepared ranging from 1.56 nM to 0.01 nM. Stable HEK NFκB-Luc-GFP Receptor X cells were thawed and washed with 10 ml of PBS by centrifugation for 5 minutes at 350 g. The supernatant was discarded and the pellet was resuspended in Tag-lite® reaction buffer to have 1 Mio cells/ml. 0.05 ng/µl WGA-Terbium was added to the cell suspension and incubated at room temperature for 30 minutes. Afterwards the cells were washed again and resuspended in an appropriate volume of Tag-lite® reaction buffer to have a final concentration of 1 Mio cells/ml.

10 µl of the resuspended WGA-Terbium labeled cells were mixed with 10 µl of Tag-lite® reaction buffer in a 384-well-plate. The terbium signal was determined in triplicates at a wavelength of 615 nm using the Victor3™ plate reader. The assay was pipetted using 10 µl of cells with a certain terbium signal, 5 µl of anti-human-IgG-d2 and for the titration 5 µl of a dilution of the antibody. As a blank, 10 µl of the cells, 5 µl of the secondary antibody and 5 µl of buffer was pipetted. The assay was pipetted in triplicates in a 384-well-plate and measured after 0 h, 2 h and 4 h of incubation at room temperature with the Tecan Infinite® M1000 Pro plate reader. The evaluation of the raw data was done as described above.

Results

Figure 15:
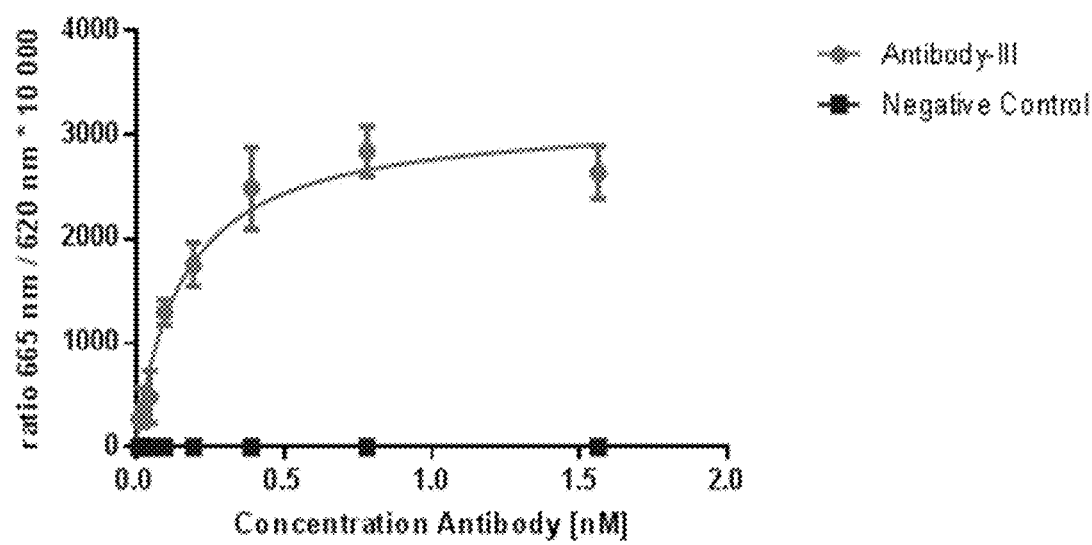
FIG. 15. WGA-HTRF indirect binding assay with Antibody-III to Receptor X expressing HEK NFκB-Luc-GFP cells. Antibody-V served as a negative control. Both antibodies were diluted ranging from 1.56 nM to 0.01 nM in a two-fold dilution series. The d2-labeled secondary antibody was used in a concentration of 75 nM. The binding curve was fitted by nonlinear regression with Graph Pad Prism 6.0.

The stably transfected cells were incubated with the terbium-conjugated lectin WGA and an indirect HTRF assay was set-up by using anti-human-IgG-d2 as an acceptor labeled secondary antibody (FIG. 15).

In FIG. 15 a binding signal of Antibody-III was detected compared to the negative control. The measured values were fitted equally with the Tag-lite® experiments, so that the KD value can be determined and compared. The KD value in this experiment was 0.15 nM±0.03 nM (R2=0.97).

Example 5: Combination Assay

For the combination assay, a two-fold dilution series of Antibody-III in FluoroBrite DMEM+10% FBS was prepared ranging from 200 nM to 0.1 nM. This leads to concentrations ranging from 40 nM to 0.02 nM final per well. The anti-human-IgG-d2 detection antibody was diluted in the same medium to a final concentration of 120 nM per well. HEK NFκB-Luc-GFP cells which were transiently supertransfected with the SNAP-Receptor X plasmid and labeled with terbium were used. The cell line was thawed and washed with 10 ml of PBS by centrifugation for 5 minutes at 350 g. The supernatant was discarded and the pellet was resuspended in FluoroBrite DMEM+10% FBS. The assay was pipetted in a 384-well-plate using 10 000 cells in 15 μl medium, 5 μl of anti-human-IgG-d2 and 5 μl of the dilution series of the antibody per well. As a blank, 15 μl of the cells, 5 μl of the secondary antibody and 5 μl of buffer was pipetted. All measurements were done in triplicates. The plate was measured after 0 h, 2 h and 4 h incubation at 37° C. and 5% CO2 with the Tecan Infinite® M1000 Pro plate reader. After 24 h of incubation, 10 μl of supernatant was removed to have a final volume of 15 μl per well remaining. 15 μl of ONE-Glo™ Luciferase reagent was added per well. After 5 minutes of incubation in the dark, light emission was measured by the SpectraMax M5/M5e plate reader with 500 ms integration time. As a blank, the signal of the lysed non-activated cells with the luciferase reagent was subtracted.

Results

Figure 16:
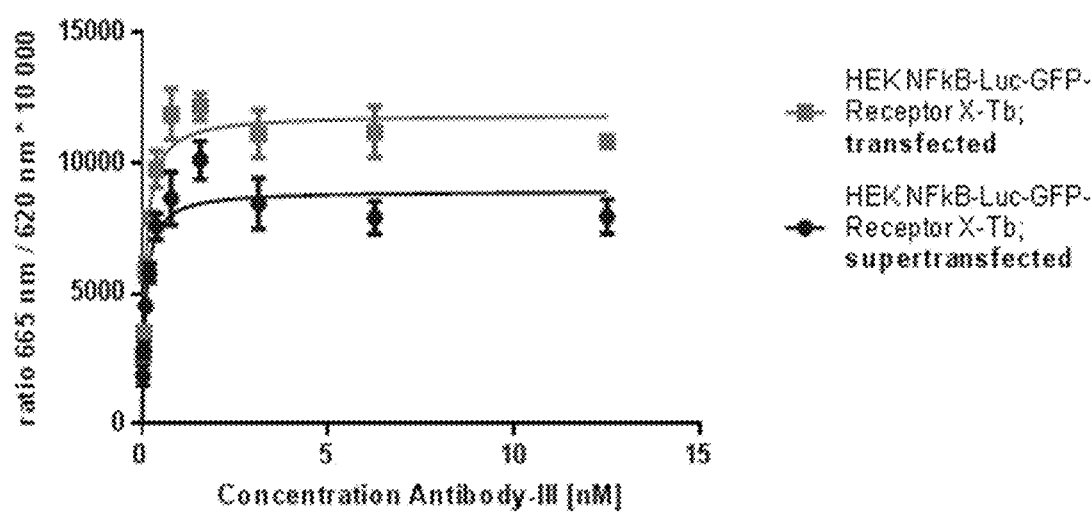
FIG. 16. Indirect Tag-lite® binding assay with Antibody-III for transiently supertransfected and transiently transfected Receptor X expressing HEK NFκB-Luc-GFP cells. All antibodies were diluted ranging from 12.5 nM to 0.02 nM in a two-fold dilution series. The d2-labeled secondary antibody was used in a concentration of 75 nM. The binding curve was fitted by nonlinear regression with Graph Pad Prism 6.0.

Evaluation of a Cell Line Suitable for Combining Functionality and Binding Assessment A new approach is to "transiently supertransfect" stably transfected HEK NFκB-Luc-GFP-Receptor X cells. This means the plasmid encoding for SNAP-Receptor X was used to transfect the HEK NFκB-Luc-GFP-Receptor X cells again with Receptor X fused to the SNAP-tag®. Afterwards, the cells were labeled with terbium and could be used for a normal indirect Tag-lite® binding experiment (FIG. 16). The transiently transfected cells were used as a control as they showed good binding with Antibody-III in the initial experiments. FIG. 16 shows that there was a lower ratio for the transiently supertransfected cells compared to the transiently transfected cells. However, the signal was high enough to obtain a nice curve fit and determine the KD value. The KD was the same for both cell types with 0.09 nM±0.02 nM (R2=0.92) was and also 0.09 nM±0.02 nM (R2=0.96) for the HEK NFκB-Luc-GFPReceptor X-Tb supertransfected and transfected cells, respectively.

Thus, those supertransfected cells have the potential to be used as a model in an assay combining functionality and binding assessment.

Figure 17:
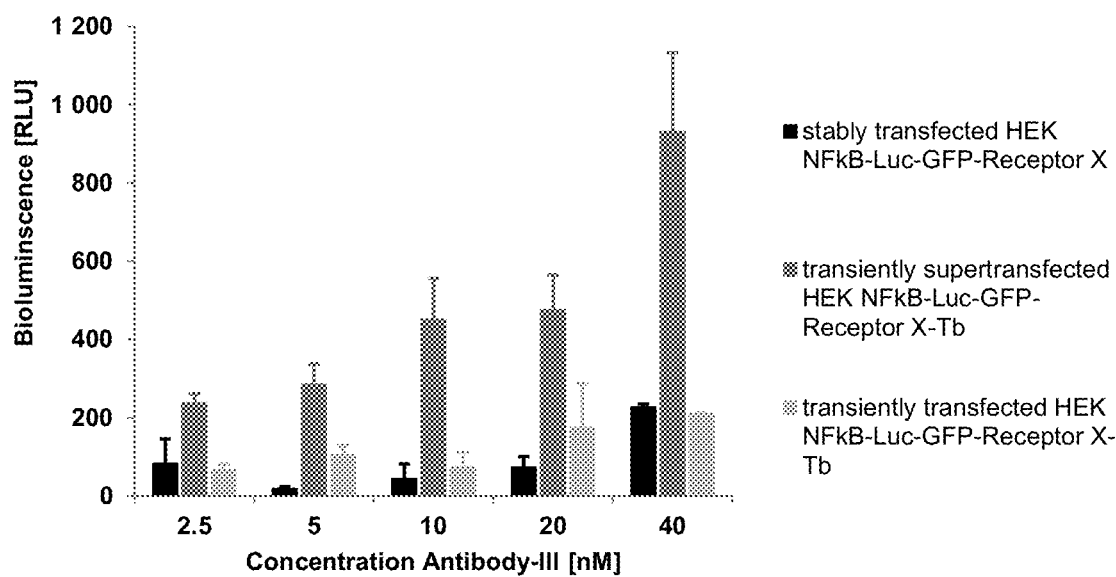
FIG. 17. Stably transfected, transiently transfected and transiently supertransfected Receptor X expressing HEK NFκB-Luc-GFP cells were tested in a ONE-Glo™ luciferase assay system after 24 h of incubation. The NFκB pathway was activated through Antibody-III in a two-fold dilution series ranging from 40 to 2.5 nM. Anti-hu IgG Fcγ-specific goat IgG F(ab)2 as a secondary antibody was added in a four-fold molar extent compared to the primary antibody.

In the final experiments before combining the Tag-lite® assay with the luciferase assay, the optimal concentrations of the primary and secondary antibodies were found out in a luciferase assay. First, Antibody-III as the primary antibody was titrated in five concentrations between 2.5 and 40 nM, whereas the ratio from the primary to the secondary antibody was kept constant in a 1:4 ratio. Besides the stably and transiently transfected Receptor X expressing HEK NFκB-Luc-GFP cells, also the transiently supertransfected cells were tested (FIG. 17).

Figure 18:
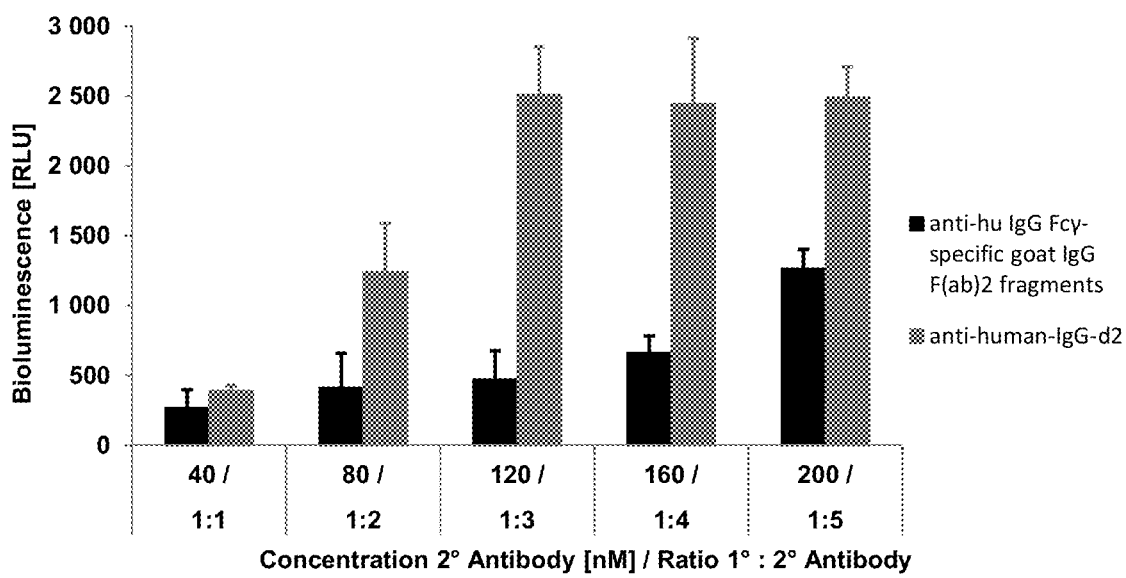
FIG. 18. Transiently supertransfected Receptor X expressing HEK NFκB-Luc-GFP cells were tested in an ONE-Glo™ Luciferase assay system after 24 h of incubation. The NFκB pathway was activated through Antibody-III in a concentration of 40 nM. Anti-hu IgG Fcγ-specific goat IgG F(ab)2 and anti-hu-IgG-d2 as secondary antibodies were tested in ratios between 1:1 and 1:5 (1°: 2° antibody).

The transiently supertransfected cells show a very high bioluminescent signal compared to the other two cell lines. Additionally, among all cell lines it can be clearly seen that a concentration of 40 nM of the primary antibody showed the best result. Thus, this concentration for Antibody-III was kept constant in the following assay, whereas the ratios to the secondary antibody have been changed from a 1:1 ratio to a 1:5 ratio. Moreover, the secondary antibody which was usually used in a luciferase assay (anti-human IgG Fcγ-specific goat IgG F(ab)2 fragments) for crosslinking was compared to the d2-labeled secondary antibody (anti-human-IgG-d2) which was commonly used in a Tag-lite® experiment (FIG. 18). FIG. 18 shows that the bioluminescent signal was stronger when crosslinking with the d2-labeled anti-human-IgG. There, a concentration of 120 nM (1:3 ratio) for the secondary antibody is already enough. For the anti-hu IgG Fcγ-specific goat IgG F(ab)2, a concentration of 200 nM (1:5 ratio) showed the best result.

Combination Assay with Final Conditions

All necessary parameters to combine a binding assay with a functionality assay were evaluated and defined.

Figure 19:
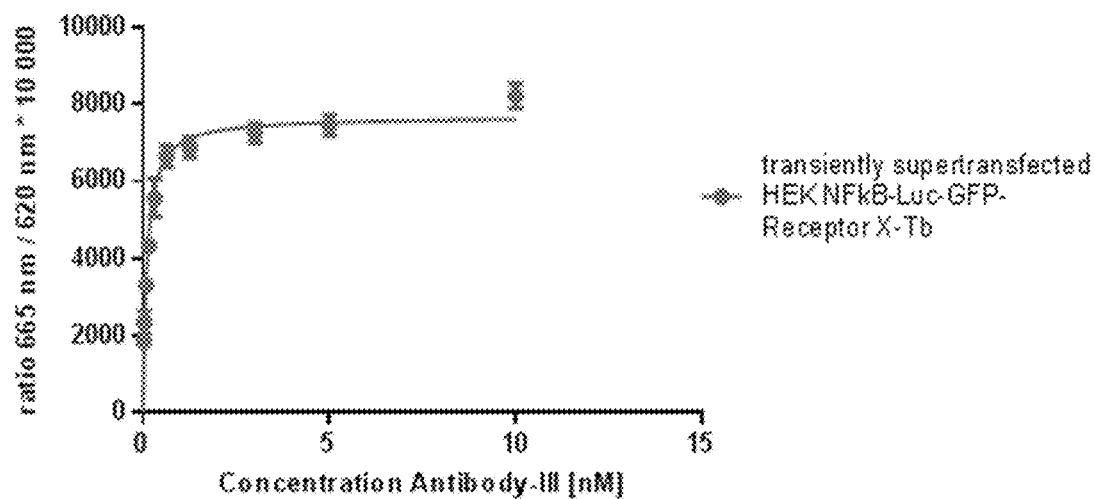
FIG. 19. Indirect Tag-lite® binding assay with Antibody-III to transiently supertransfected Receptor X expressing HEK NFκB-Luc-GFP cells. Antibody-III was diluted ranging from 40 nM to 0.02 nM in a two-fold dilution series. The d2-labeled secondary antibody was used in a concentration of 120 nM. The binding curve was fitted by nonlinear regression with Graph Pad Prism 6.0.
Figure 20:
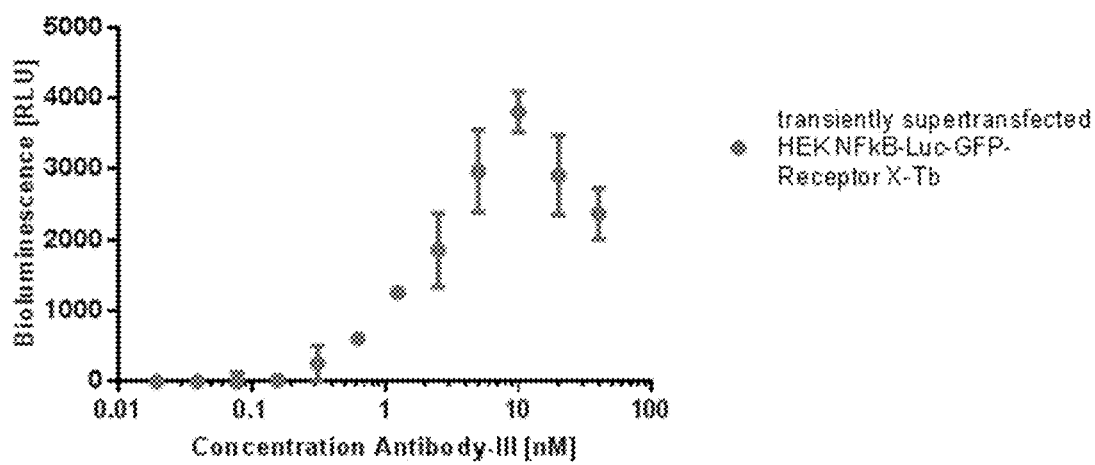
FIG. 20. Transiently supertransfected Receptor X expressing HEK NFκB-Luc-GFP cells were tested in a ONE-Glo™ luciferase assay system after 24 h of incubation. The NFκB pathway was activated through Antibody-III in a two-fold dilution series ranging from 40 to 0.02 nM. Anti-human-IgG-d2 as a secondary antibody was added in a three-fold molar extent compared to the primary antibody.

Transiently supertransfected Receptor X expressing HEK NFκB-Luc-GFP cells were used to perform the combination assay. Therefore, 10 000 cells per well were mixed with Antibody-III and the secondary antibody in a 384-well-plate. An indirect Tag-lite® binding assay was performed over a period of 4 h (FIG. 19). 24 h after activation of Receptor X, the cells were lyzed using the ONE-Glo™ luciferase reagent. As this reagent also contains the luciferase substrate, the light released from the oxidation of luciferin to oxyluciferin was measured by the luminometer (FIG. 20). The KD determined in FIG. 28 was 0.10 nM±0.01 nM (R2=0.98) for the HEK NFκB-Luc-GFP-Receptor X-Tb supertransfected cells.

FIG. 20 shows that with an increasing concentration up to 10 nM of the primary antibody, the luminescent signal was increasing, too. Thus, the combination of the primary and secondary antibody resulted in an activation of the NFκB pathway.

In conclusion, Antibody-III was able to bind to Receptor X and it also showed a good functionality.

While there are shown and described presently preferred embodiments of the invention, it is to be distinctly understood that the invention is not limited thereto but may be otherwise variously embodied and practiced within the scope of the following claims.

Discussion

Evaluation of the Cell Lines

Prior to transfection of the SNAP-Receptor X plasmid, HEK NFκB-Luc-GFP and HeLa NFκB-Luc were tested in a luciferase assay. The signal of the HEK NFκB-Luc-GFP cells was significantly higher than it was detected with the HeLa NFκB-Luc cells, but those two cell lines should not be compared, since their growth rates are totally different. The same amount of cells was seeded the day before activation. Since HEK NFκB-Luc-GFP cells divide much faster, more cells could be activated the next day. For further experiments, HeLa NFκB-Luc cells have to be seeded in a higher cell number than HEK NFκB-Luc-GFP cells. However, since both cell lines could be activated well, they were used for transfection of the target receptor fused to the SNAP-tag®.

Protein-Protein Interaction Studies

In an indirect Tag-lite® binding assay, Antibody-I was compared to Antibody-II. The difference between those antibodies was an exchange of one amino acid in the complementarity determining regions (CDRs) of the light chain of Antibody-I. This must be the reason why Antibody-I binds to its target unlike Antibody-II.

Instead of using Tag-lite® reaction buffer, also FluoroBrite DMEM/10% FBS and DMEM/10% FBS can be used. PBS in contrast or DMEM do not support the binding of the antibody to the target receptor. DMEM and DMEM/10% FBS in comparison was a good example, that FBS increases the binding. FBS as a media supplement delivers nutrients for the cells and contains growth factors. Probably the increase in binding when using medium containing FBS was just due to a lower cell death or better cell growth. The explanation why PBS decreases the binding was probably the same and when incubating the cells 4 h in PBS they might start binding. The composition of Tag-lite® reaction buffer is not known, but it seems that it supported binding of two proteins and kept the cells alive.

After a transient transfection of the SNAP-Receptor X plasmid on HEK NFκB-Luc-GFP cells, the receptor stability was tested by performing Tag-lite® assays every day after thawing the cells. A strong decrease from day 0 (directly after thawing) to day 1 was observed. But this does not necessarily mean that the receptors on the cell surface got lost. The cells were just transiently transfected, thus, after proliferation the daughter cells do not have the gene for expressing Receptor X. Since the assay was performed by using every day the same amount of cells, it could be that many of the cells used in the assay at day 1 are those daughter cells which do not have this receptor. Receptor X expressing cells at day 2 and 3 were totally overgrown by non-Receptor X expressing daughter cells. This assumption also fits to the daily measurements of the terbium signal and the viability. At day 0, a high terbium signal was determined while the viability was low. Thus, directly after freezing the cells were not that healthy, but most of the cells expressed Receptor X. From day to day the cells proliferated resulting in more healthy daughter cells but without having the labeled target receptor on their cell surface. Another assumption would be internalization and degradation of the receptors.

For the combination assay of binding and functionality, this result was not of any concern, since the cells are activated directly after freezing. Then, the binding was measured over a period of 4 h and for the measurement of the functionality after a few hours the presence of the receptors on the cell surface does not play any role. The period of incubation after activating the cells and measuring functionality was necessary to obtain a high luciferase expression.

Luciferase Assay

Antibody-I which showed a good binding in the Tag-lite® assay was used for the initial luciferase assay after the transient transfection and labeling. In addition, the NFκB pathway was also tried to be activated by TNFα. The activation by TNFα worked quite well. This demonstrated that the transfection and labeling of the cells did not modify the cells and the NFκB pathway still works. There were also cells used in the assay without activation that served as a blank which was subtracted from the signal. This confirmed that the cells do not express any luciferase constitutively. Only a weak luminescent signal was observed when activating the cells with Antibody-I and the secondary antibody. This was a good example to show the necessity to perform a combination assay, since Antibody-I was determined to be one of the best binders.

In another Luciferase assay, two different incubation times (6 h and 48 h) were compared using stably and transiently transfected Receptor X expressing HEK NFκB-Luc-GFP cells. It was clearly seen that more luciferase was expressed in the stably transfected cells after 48 h which resulted in a stronger luminescent signal. Unfortunately, the transiently transfected cells showed only a very weak luminescent signal. The transiently transfected cells express Receptor X only fused to a SNAP-tag®. Since the activation of the NFκB pathway occurs only upon oligomerization of the ReceptorX, the size of the SNAP-tag® (20 kDa) might lead to steric hindrance and inhibition of the oligomerisation.

Indirect WGA-HTRF

WGA enables to perform cell based protein-protein interaction measurements in a new way by avoiding the direct labeling of receptors expressed on the cell surface. An approach to avoid the SNAP-tag® and to allow the use of stably transfected cells for the combination assay was to label them with terbium by using WGA. Thus, an indirect HTRF assay could be performed. The KD value was with 0.15 nM±0.03 nM in the same range than it was determined in the normal Tag-lite® experiments on transiently transfected Receptor X expressing HEK NFκB-Luc-GFP cells. Thus, WGA as a labeling tool would also be useful in this set-up to perform a combination assay but could not be further evaluated due to time limitations.

Evaluation of a Cell Line Suitable for Combining Functionality and Binding Assessment A transient supertransfection of stably transfected HEK NFκB-Luc-GFP-Receptor X cells was the second approach, which enables to perform a normal indirect Tag-lite® binding experiment. Besides testing them in a binding assay, also the luciferase assay was evaluated with this cell line. Therefore, those cells were used to find out the optimal concentration of the primary antibody and simultaneously they were compared to transiently and stably transfected Receptor X expressing HEK NFκB-Luc-GFP cells. For every concentration of Antibody-III, the supertransfected cells show clearly the strongest luminescent signal. One reason why the supertransfected cells show a higher signal compared to stable cells is that there were more target receptors present on the cell surface. Thus, more antibodies could bind and more crosslinking could take place, resulting in a stronger activation of the NFκB pathway. The signal of the stably transfected cells was in general in this assay extremely low. The reason was probably a wrong handling in passaging cells. If they are splitted very late and the cells have a high confluency, it was observed that the cells cannot be activated that well. Either some cells lost the receptors on their cell surface or they downregulated signaling events somehow.

It is also assumed that the signal of the transiently supertransfected cells was higher than of the transiently transfected cells due to steric hindrance. The supertransfected cells overexpress Receptor X on their cell surface. Some of them are fused to a SNAP-tag®, since they were transiently transfected with a SNAP-Receptor X plasmid, but some of them do not have the SNAP-tag®, since the stably transfected Receptor X expressing HEK NFκB-Luc-GFP cell line was used for the transient transfection of SNAP-Receptor X. Probably, the activation of this cells was better because of the reason that there was less steric hindrance when oligomerisation of receptors carrying the SNAP-tag® with receptors without SNAP-tag® took place.

In addition, two secondary antibodies were compared on transiently supertransfected Receptor X expressing HEK NFκB-Luc-GFP cells. The one which was usually used in a luciferase assay (anti-human IgG Fcγ-specific goat IgG F(ab)2 fragments) showed a lower signal compared to the d2-labeled secondary antibody (anti-human-IgG-d2) which was commonly used in a Tag-lite® experiment. A possible reason is that the anti-human-IgG-d2 is a polyclonal antibody. Polyclonal antibodies are ideally suited as a secondary antibody, since those antibodies are not restricted to one epitope on their target and can therefore crosslink various constructs at the same time. The formerly used secondary antibody is a monoclonal (Fab)2 fragment binding only to one specific epitope which is not ideal for achieving a good hypercrosslinking.

Finally, the transiently supertransfected Receptor X expressing HEK NFκB-Luc-GFP cells were used as a model for the combination assay.

Conclusion

It was possible to align the parameters of both individual assays, luciferase and Tag-lite® assay, to develop a new assay, combining both in one well. For instance, the Tag-lite® assay can be performed at 37° C. instead of incubation at room temperature. Additionally, medium could be used instead of Tag-lite® reaction buffer and also the amount of cells that are seeded per well can vary in a large extent without changing the results. Moreover, down-scaling of the ONE-Glo™ Luciferase assay system worked well. Thus, the combination assay could be performed in a 384-well-plate, which was also used for the Tag-lite® experiments in the past. Advantages of this scale are not only the lower amounts of reagents that are needed, resulting in a drop in the overall costs, but also its suitability for performing HTS.

The final combination assay was performed with transiently supertransfected cells, since there was no stable cell line available containing the SNAP tag additionally to the target receptor. For future experiments using a combination assay, it would be possible to generate cell lines with that tag or to supertransfect them, as well. In addition, cells without the SNAP-tag® could be used by performing a WGA-HTRF.

In conclusion, the development of the combination assay is not only useful for the NFκB signaling pathway, there is also a potential to extend the assay to other functionality readouts, e.g. cytokine release or additional signaling pathways.

Example 6: AlphaScreen

For the evaluation of the different assays huDR5 specific antibody Drozitumab was used. HuDR5 was expressed by HEK EBNA cells. For the AlphaScreen based method, biotinylated WGA was bound to Streptavidin donor beads (PerkinElmer) and binding of Drozitumab to DR5 was detected with ProtA acceptor beads (PerkinElmer) which bind to the Fc portion of antibodies.

It is noteworthy that all pipetting steps and measurements were done in a dark room because the beads are light sensitive.

Defining the Assay Window of the AlphaScreen

To define the assay window an AlphaScreen assay was done with 1.4 nM WGA-biotin and 10000 cells. PerkinElmer recommended a concentration of 10 µg/ml of each bead, acceptor and donor. First, 10 µg/ml of Streptavidin donor beads were mixed with 1.4 nM of WGA-biotin and incubated for 30 min. Meanwhile, the dilution row of Drozitumab was prepared starting with a concentration of 1200 nM to 0.0011 nM in 1 in 4 dilution steps. The HEK EBNA cells expressing huDR5 SNAP Tag were thawed, washed with 10 ml of 1×PBS and centrifuged for 8 min and 350 g. The supernatant was discarded. The pellet was resuspended in an appropriate volume to get 1 mio cells/ml. The Streptavidin beads labeled with WGA-biotin were added to the resuspended cells and incubated for 30 min at room temperature. While incubating the cells, 5 µl of the diluted antibodies were transferred to a 384-well plate in duplicates and 5 µl of the ProteinA acceptor beads (10 µg/ml) were added. The 384-plate was incubated for 30 min. The cells were filled up to 10 ml with 1× reaction buffer and centrifuged for 8 min at 350 g. The supernatant was discarded and the pellet was resuspended in an appropriate volume with 1× reaction buffer to get 1.0 mio cells/ml. 10 µl of the WGA-streptavidin beads labeled cells were transferred to each well of a 384-well plate. The blank was prepared with 10 µl WGA-streptavidin labeled cells, 5 µl of ProteinA acceptor beads and 5 µl of 1× reaction buffer. All measurements were done in duplicates. The 384-well plate was measured after 1 h, 2 h, 3 h and 4 h with the Tecan M1000 Pro reader using the AlphaScreen template. The raw data was evaluated in Excel by subtracting the blank and further analyzing it in GraphPad Prism.

Evaluation of Cell Number and WGA-Biotin Per Well

First, 10 µg/ml of Streptavidin donor beads were mixed with either 1.4 nM or 2.8 nM of WGA-biotin and incubated for 30 min. Meanwhile, the dilution row of Drozitumab was prepared starting with a concentration of 6.25 nM to 0.020 nM in 1 in 2 dilution steps. The HEK EBNA cells expressing huDR5 SNAP Tag were thawed, split in two 15 ml Falcon tubes and washed with 10 ml of 1×PBS and centrifuged for 8 min and 350 g. The supernatant was discarded. The pellet of the two vials was resuspended in an appropriate volume to get 1 mio cells/ml or 2.0 mio cells/ml. The Streptavidin beads labeled with WGA-biotin were transferred to the resuspended cells and incubated for 30 min at room temperature. While incubating the cells, 5 µl of the diluted antibodies were transferred to a 384-well plate in duplicates and 5 µl of the ProteinA acceptor beads (10 µg/ml) were added. The 384-plate was incubated for 30 min. The cells were filled up to 10 ml with 1× reaction buffer and centrifuged for 8 min at 350 g. The supernatant was discarded and the pellet was resuspended in an appropriate volume with 1× reaction buffer to get 1.0 mio cells/ml and 2.0 mio cells/ml. 10 µl of the WGA-streptavidin beads labeled cells were transferred to the 384-well plate. The blank was prepared with 10 µl WGA-streptavidin labeled cells, 5 µl of ProteinA acceptor beads and 5 µl of 1× reaction buffer. All measurements were done in duplicates. The 384-well plate was measured after 1 h, 2 h, 3 h and 4 h with the Tecan M1000 Pro reader using the AlphaScreen template. The raw data was evaluated in Excel by subtracting the blank and further analyses in GraphPad Prism.

Evaluation of Different Acceptor/Donor Pairs

To define which acceptor/donor pair works best, an AlphaScreen assay was carried out with 2.8 nM WGA-biotin and 20000 cells. First, 10 µg/ml of Streptavidin donor beads or 10 µg/ml of Streptavidin acceptor beads were mixed with 2.8 nM of WGA-biotin and incubated for 30 min. Meanwhile, the dilution row of Drozitumab and AbY was prepared starting with a concentration of 25 nM to 0.024 nM in 1 in 2 dilutions. The HEK EBNA cells expressing huDR5 SNAP Tag were thawed and split in two 15 ml Falcon tubes, one for each Streptavidin bead (donor or acceptor). The cells were washed with 10 ml of 1×PBS and centrifuged for 8 min and 350 g. The supernatant was discarded. The pellet of the two vials was resuspended in an appropriate volume to get 2.0 mio cells/ml. The Streptavidin beads labeled with WGA-biotin were transferred to the resuspended cells and incubated for 30 min at room temperature. While incubating the cells, 5 µl of the diluted antibodies were transferred to a 384-well plate in duplicates and either 5 µl of the ProteinA donor beads (10 µg/ml) or ProteinA acceptor beads (10 µg/ml) was added. The 384-plate was incubated for 30 min. The cells were filled up to 10 ml with 1× reaction buffer and centrifuged for 8 min at 350 g. The supernatant was discarded and the pellet of both vials was resuspended in an appropriate volume with 1× reaction buffer to get 2.0 mio cells/ml. 10 µl of the WGA-streptavidin beads labeled cells were transferred to the 384-well plate. The blank was prepared with 10 µl WGA-streptavidin labeled cells, 5 µl of ProteinA beads and 5 µl of 1× reaction buffer. All measurements were done in duplicates. The 384-well plate was measured after 1 h, 2 h, 3 h and 4 h with the Tecan M1000 Pro reader using the AlphaScreen template. The raw data was evaluated in Excel by subtracting the blank and analyzed in GraphPad Prism.

AlphaScreen with Final Conditions

First, 10 μg/ml of Streptavidin acceptor beads were mixed with 2.8 nM of WGA-biotin and incubated for 30 min. Meanwhile, the dilution row of Drozitumab was prepared starting with a concentration of 2.5 nM to 0.020 nM. The dilution was done in 1 in 2 dilution steps. The HEK EBNA cells expressing huDR5 SNAP Tag were thawed, washed with 10 ml of 1×PBS and centrifuged for 8 min and 350 g. The supernatant was discarded. The pellet was resuspended in an appropriate volume to get 2.0 mio cells/ml. The Streptavidin beads labeled with WGA-biotin were transferred to the resuspended cells and incubated for 30 min at room temperature. While incubating the cells, 5 μl of the diluted antibodies were transferred to a 384-well plate in duplicates and 5 μl of the ProteinA donor beads (10 μg/ml) was added. The 384-plate was incubated for 30 min. The cells were filled up to 10 ml with 1× reaction buffer and centrifuged for 8 min at 350 g. The supernatant was discarded and the pellet was resuspended in an appropriate volume with 1× reaction buffer to get 2.0 mio cells/ml. 10 μl of the WGA-streptavidin beads labeled cells were transferred to the 384-well plate. The blank was prepared with 10 μl WGA-streptavidin labeled cells, 5 μl of ProteinA donor beads and 5 μl of 1× reaction buffer. All measurements were done in triplicates. The 384-well plate was measured after 1 h, 2 h, 3 h and 4 h with the Tecan M1000 Pro reader using the AlphaScreen template. The raw data was evaluated in Excel by subtracting the blank. $K_D$ value was calculated by nonlinear regression.

Evaluation of the AlphaScreen Raw Data

The data was normalized to the background. The normalized data were evaluated by nonlinear regression to determine the binding curve and the $K_D$ value by the software GraphPad Prism 6.0. The binding curve was fitted using a sigmoidal dose-response (variable slope) according to the following equation:

$$Y = \text{Bottom} + \frac{(\text{Top} - \text{Bottom})}{1 + 10^{(logEC50-X)*Hill\ Slope}}.$$

The $K_D$ was determined using a one site binding model according to the following equation:

$$Y = \frac{B_{max} * X}{(K_D + X)}.$$

Results

Defining the Assay Window of the AlphaScreen

In the first assay the number of huDR5 expressing HEK EBNA cells per well, the amount of biotinylated WGA per well and the incubation time of WGA-biotin with the cells was adopted from the WGA-HTRF. 10000 cells and 1.4 nM WGA-biotin were used per well. Both antibodies were diluted starting from 300 nM to $3.0*10^4$ nM final in well in 1 in 4 dilutions.

The first test of the AlphaScreen assay showed that the idea of the assay setup should work. However, the curve of Drozitumab showed a relatively small assay window starting with a concentration of 0.018 nM to 19 nM.

Evaluation of Cell Number and WGA-Biotin Per Well

To improve the assay in a next step the cell number was set to 10000 and 20000 cells per well and the amount of WGA-biotin was set to either 1.4 nM or 2.8 nM per well. To get a better assay window the dilution steps were decreased to 1 in 2 rather than 1 in 5 starting with a concentration of 50 nM final in the well. Both antibodies were diluted starting from 50 nM to 0.049 nM final in well in 1 in 2 dilutions.

Both assay setups using 1.4 nM WGA-biotin per well showed only a slight or no binding signal. The one with 10000 cells per well and 2.8 nM WGA-biotin per well showed a weak binding curve. The best result were obtained with 20000 cells and 2.8 nM WGA-biotin per well.

Evaluation of Different Acceptor/Donor Pairs

To perform an AlphaScreen assay it is possible either to use Streptavidin donor beads with ProtA acceptor beads or Streptavidin acceptor beads with ProtA donor beads. To find out the best donor/acceptor pair they were compared to each other Both antibodies were diluted starting from 1.6 nM to 0.006 nM final in well in 1 in 2 dilutions. The two different donor/acceptor pairs showed nearly the same binding curve. Even the difference in their $R^2$ value was almost the same. The assay measured with Streptavidin donor beads and ProtA acceptor beads had a $R^2$ value of 0.99 and the assay measured with Streptavidin acceptor beads paired with ProtA acceptor beads had a $R^2$ value of 0.99.

AlphaScreen with Final Conditions

The result of the evaluation of the AlphaScreen was to run the AlphaScreen with the following set up (table 2).

TABLE 2

Finally evaluated parameters to perform a AlphaScreen assay.

| Parameter | Conditions |
| --- | --- |
| WGA-biotin per well | 2.8 nM |
| Cell count per well | 20000 cells |
| Amount of streptavidin donor beads | 10 μg/ml |
| Amount of ProtA acceptor beads | 10 μg/ml |
| Incubation time of streptavidin acceptor beads and WGA-biotin | 30 min |
| Incubation time of acceptor beads labeled WGA and cells | 30 min |
| Incubation time of antibody dilutions with ProtA acceptor beads | 30 min |

Figure 21:
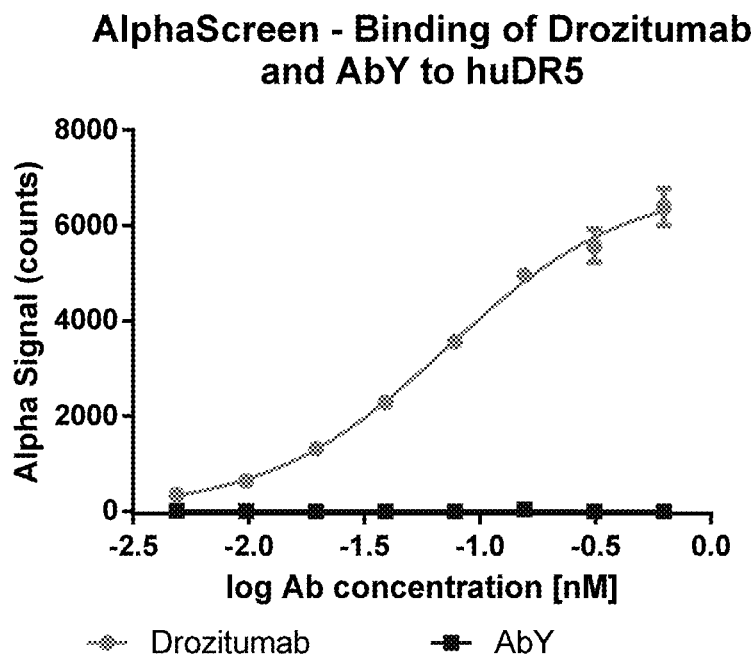
FIG. 21. AlphaScreen binding assay with Drozitumab and control antibody AbY to huDR5 expressing HEK EBNA cells. All antibodies were diluted starting from 0.63 nM to 0.05 nM final in well in 1 in 2 dilutions. (A) Sigmoidal binding curve of Drozitumab and AbY fitted by nonlinear regression. (B) Determination of the KD values of Drozitumab and AbY by nonlinear regression.
Figure 21:
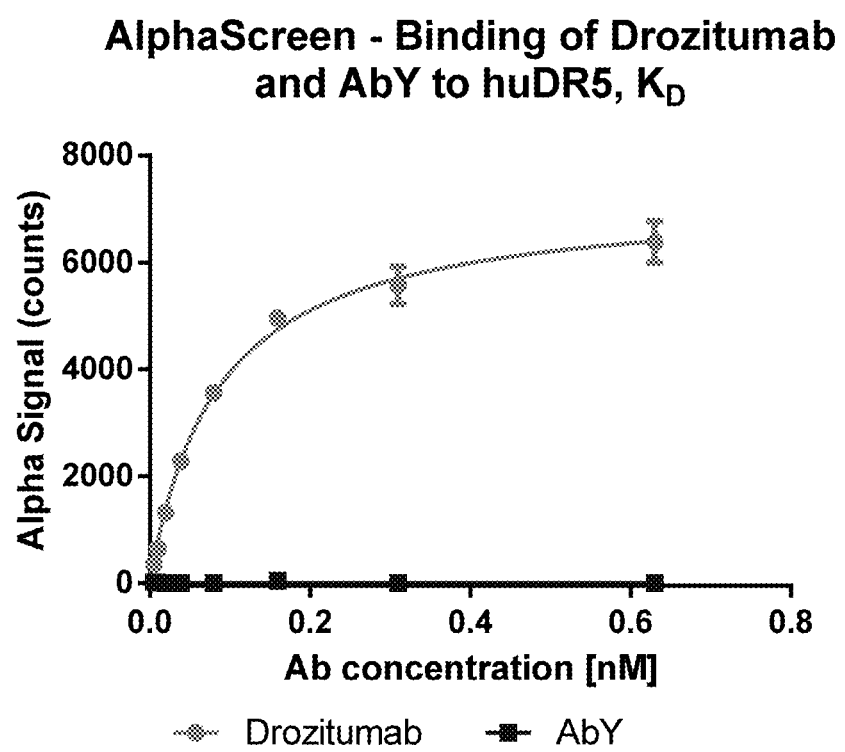

With the final condition evaluated for the AlphaScreen assay the $K_D$ value for the binding of Drozitumab to huDR5 was determined (FIG. 21).

The sigmoidal fitting of Drozitumab showed a sigmoidal shaped binding curve The $K_D$ determined by the nonlinear regression was 0.084 nM+/−0.0053 nM. Since the AbY showed no binding to huDR5 there was no $K_D$ value calculated.

Figure 22:
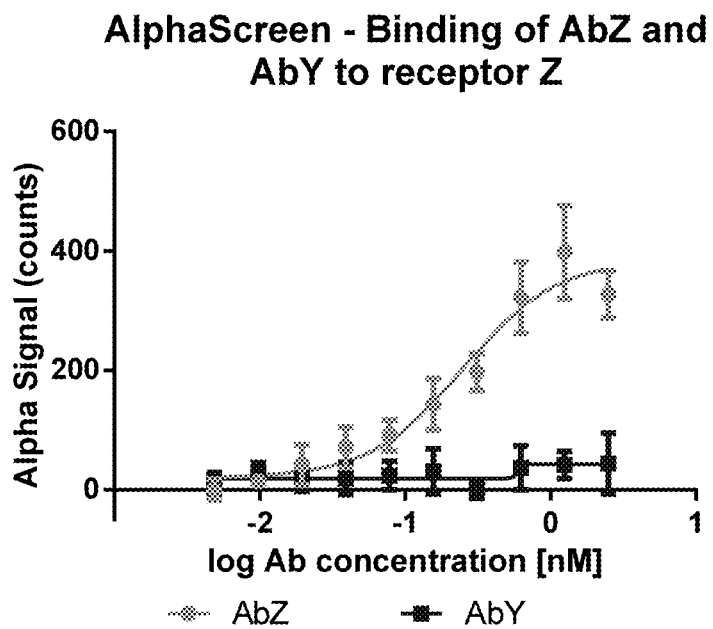
FIG. 22. AlphaScreen binding assay with AbZ and control antibody AbY to receptor Z expressing HEK EBNA cells. All antibodies were diluted starting from 2.5 nM to 0.05 nM final in well in 1 in 2 dilutions. (A) Sigmoidal binding curve of AbZ and AbY fitted by nonlinear regression. (B) Determination of the KD values of AbZ and AbY by nonlinear regression.
Figure 22:
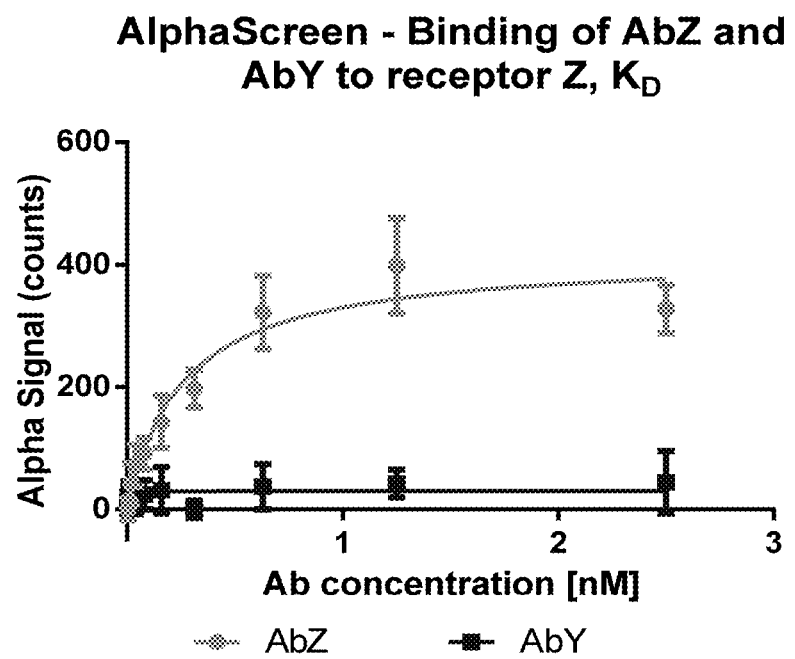

Like in the WGA-HTRF assay the result of the assay evaluation has to be confirmed using another antibody and antigen and the $K_D$ of AbZ to its target receptor Z was determined (FIG. 22).

As in the previous assays the negative control antibody AbY showed no binding. The $K_D$ value was determined by nonlinear regression. The $K_D$ of AbZ—receptor Z binding was 0.26 nM+/−0.068 nM with a $R^2$ value of 0.96. Since the AbY is a non-binder to receptor Z there was no $K_D$ value determined.

Example 7: Measuring CD3 Binding and Functionality in One Well Using a Jurkat NFAT Reporter Cell Line The Jurkat NFAT-luciferase reporter cell line is designed to monitor T cell activation that results in modulation of the nuclear factor of activator T cells (NFAT) activities.

The transcription factor NFAT has important roles in T cell development and function. In non-activated T cells, NFAT is mainly located in the cytoplasm, in a highly phosphorylated form. After antigenic T cell stimulation via TCR/CD3 receptor complex, the $Ca^{2+}$-dependent phosphatase calcineurin dephosphorylates multiple phosphoserines on NFAT, leading to its nuclear translocation and downstream gene expression of T cell activation genes.

The NFAT reporter cell was generated by clonal selection of Jurkat cells stably transfected using a NFAT-luciferase reporter vector, which contains multiple repeats of a NFAT response element and a minimal promoter upstream of the firefly luciferase coding region. The activation of NFAT has been confirmed following the induction of the reporter cell with PMA/ionomycin.

Methods

Labeling of Jurkat NFAT Reporter Cells with WGA-Tb:

Jurkat NFAT cells were spun down and resuspended in either PBS/1% FCS or growth medium to obtain 4 Mio cells/ml. Subsequently, 1 Mio cells were labeled by adding 0.5 ng/ul WGA-Terbium and incubated for 30 min at RT. Following the incubation, the cells were washed twice with PBS by centrifugation for 8 min at 280 g. Finally cells were resuspended in either PBS/1% FCS or growth medium to obtain a final number of 4 Mio cells/ml.

Binding:

A d2-labeled antibody binding to CD3 as well as a d2-labeled non-binding control IgG were resuspended in either PBS/1% FCS or growth medium and a serial dilution generated ranging from final 50-0.1 nM in 1:2 dilution steps. 40000 (10 ul) labeled cells were mixed in a 384 well with 5 ul labeled antibody and 5 ul PBS/1% FCS or growth medium. The binding assay was incubated for 5 h at 37° C. The TR-FRET signal was measured using a M1000 Pro Reader by determining the absorbance at 665 nm as well as 615 nm after a delay time of 60 sec. 40000 WGA-Tb labeled Jurkat-NFAT cells served as blank. The ratio of 665 nm/615 nm was determined for each well to normalize the specific FRET signal to the donor signal in each well. Additionally, the ratio of the blank was subtracted from the ratio of the samples before determining the KD and EC50 values in GraphPad Prism 6.0. The binding curves were fitted with nonlinear regression. Bmax and KD were determined using the "One site specific binding" model using the equation Y="("B"_"max" "*X")/("(" "K"_"D" "+X)").

Evaluation

Evaluation of the HTRF Raw Data For the analysis of the assays, the raw data were first edited by Microsoft Excel. In a HTRF assay variations in the results can occur from well to well due to the pipetting steps of the cells, medium additives and from the number of lysed cells per well. To minimize those variations, the emission of the acceptor was normalized to the emission of the donor signal in each well by calculating the ratio of 665 nm to 620 nm: "ratio=" "665 nm"/"620 nm" "*10 000". The calculated ratio values were evaluated by the software called GraphPad Prism 6.0. The binding curves were fitted with nonlinear regression. Bmax and KD were determined using the "One site—specific binding" model using the equation: "Y="("B"_"max" "*X")/("(" "K"_"D" "+X)").

Functional Assay—Luciferase Assay

CD3 signalling was measured from the same wells as the binding assay by lysing the cells after 6 h incubation at 37° C. Therefore, 5 µl assay mix was removed per well followed by adding 15µ One-Glo Luciferase reagent. After incubation for 5-10 min at RT in the dark, the luminescence signal was measured with the M1000Pro Reader with a 1000 ms integration time. As a blank, the signal of the lysed non-activated cells with the luciferase reagent was subtracted. The measurement was done in triplicates.

Results

Figure 23A:
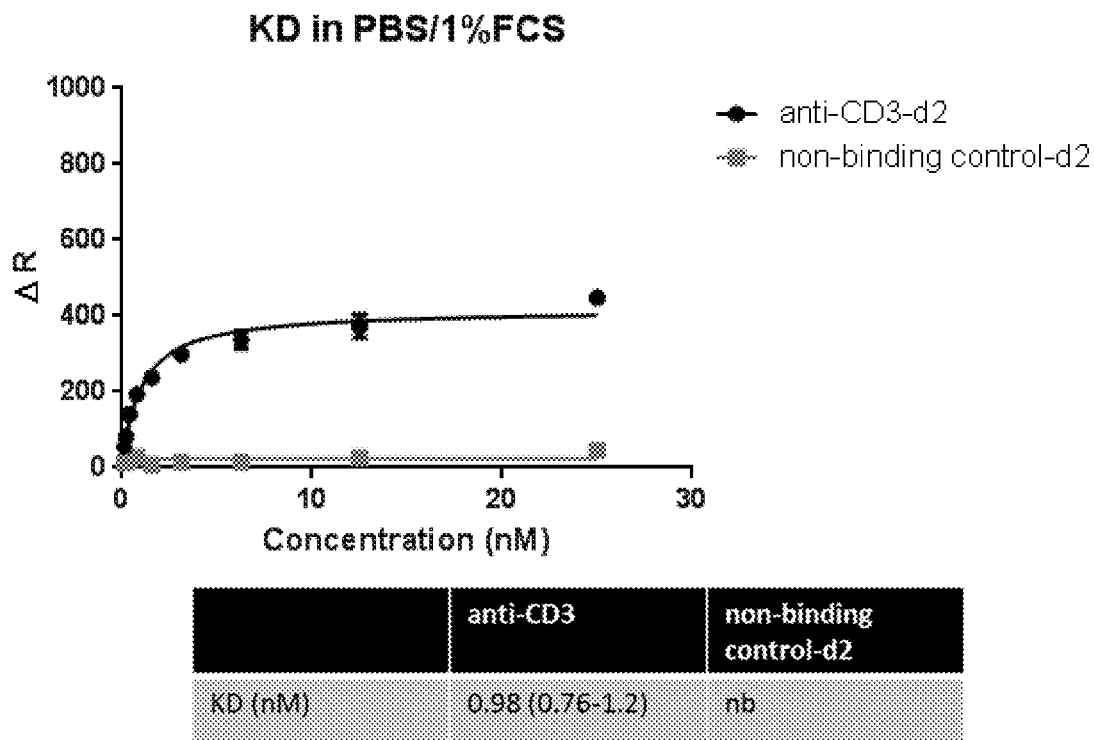
FIG. 23. WGA-FRET binding assay of anti-CD3 to CD3 expressing cells in either PBS/1% FCS (a) or growth medium (b). Additionally, a non-binding control IgG was included in both assays as negative control. The curves were fitted with Graph Pad Prism one site specific binding function.
Figure 23B:
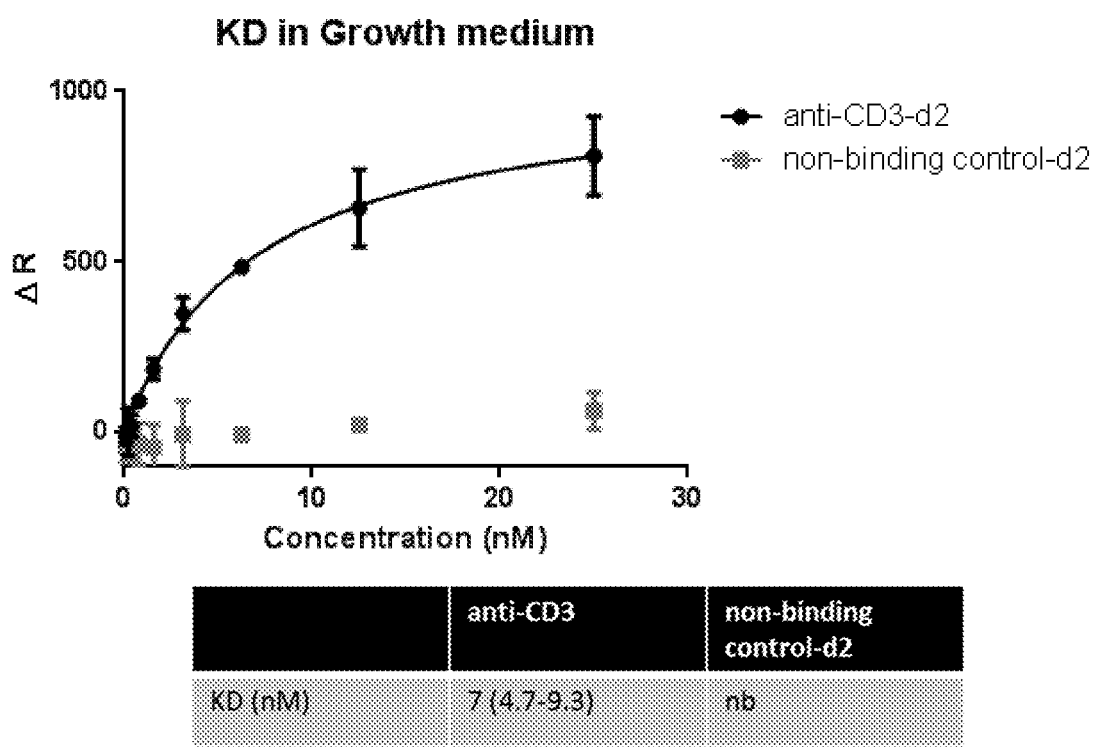

Binding Assay:

CD3 binding could be detected in growth medium (FIG. 23a) as well as PBS/1% FCS (FIG. 23b). The non-binding control does not show any binding in this assay system. The KD value for the binding of anti-CD3 to CD3 in growth medium is approximately 7 fold higher than in PBS/1% with 7 nM compared to 0.98 nM respectively.

Figure 24A:
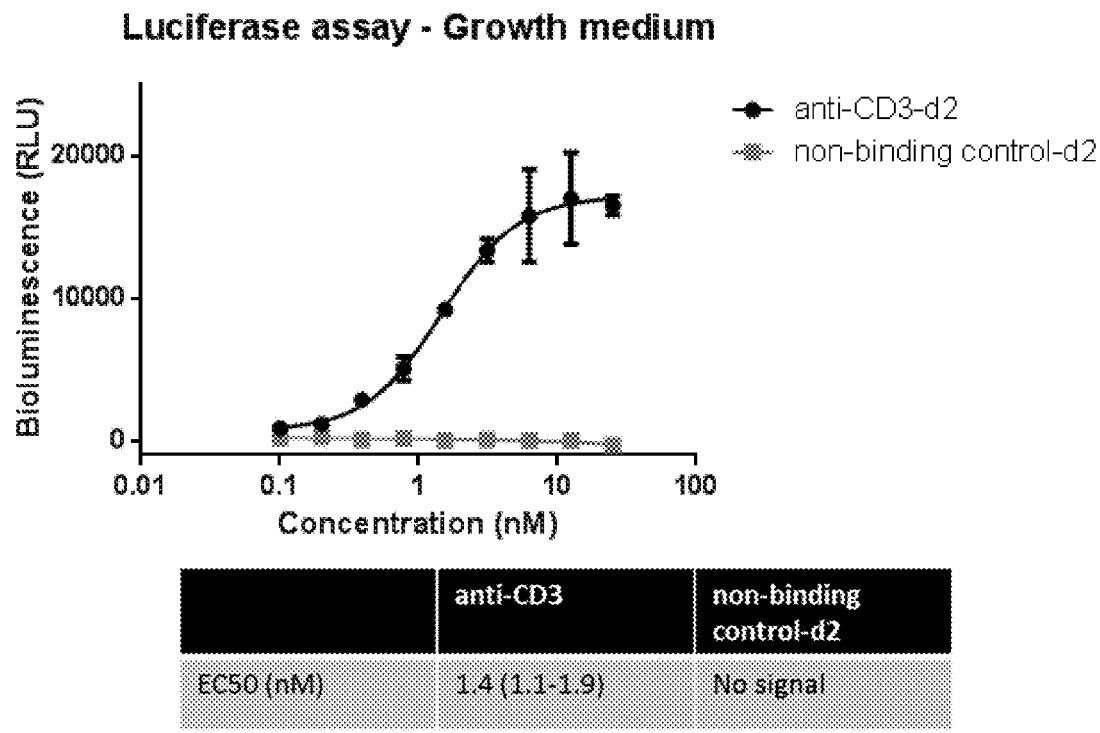
FIG. 24. Activation of the NFkB pathway upon binding of anti-CD3 either in PBS/1% FCS (a) or growth medium (b). Additionally, a non binding control IgG was used as negative control in both assays. The Luciferase activity was measured using the ONE-Glo™ Luciferase assay system. The EC50 was determined using GraphPad Prism sigmoidal dose response fit.
Figure 24B:
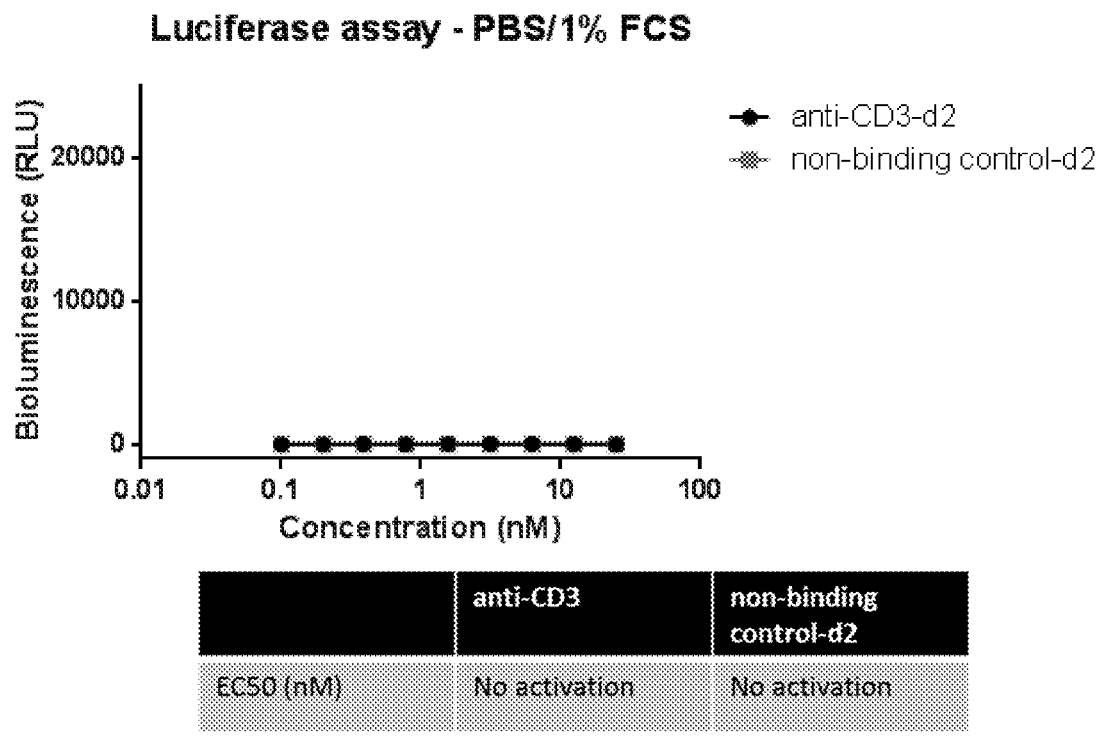

Functional Assay:

The results show that the signaling upon CD3 binding did only work in growth medium (FIG. 24a) and not in PBS/1% FCS (FIG. 24b) although similar binding was observed under both conditions. The EC50 of the luciferase activity was 1.4 nM.

CONCLUSION

The CD3 binding and functionality assessment experiment in the Jurkat NFAT reporter cell line is an additional example of an assay system where binding and functionality could be measured in a high-throughput format in one well.

---

The invention claimed is:

1. An in vitro assay method for determining the binding and functionality of a test antibody specifically binding to a target antigen comprising the following steps
   i) providing cells which
      a) expresses the target antigen on their surface,
      b) are covalently or noncovalently labelled with an energy donor compound, and
      c) comprise a reporter gene under the control of a response element of the target antigen;
   ii) adding the test antibody;
   iii) measuring the binding to the target antigen by determining the energy transfer, wherein an energy acceptor compound is covalently or noncovalently conjugated either to the test antibody or to a secondary antibody binding to the test antibody; and
   iv) determining functionality of the test antibody correlating the level of the expression of the reporter gene with the level of target antigen activation or inhibition,
   wherein the binding to the target antigen and the functionality of the test antibody is measured in the same vial, and wherein the functionality is a biological activity of the test antibody.

2. The method of claim 1, wherein the energy donor and acceptor compound are a fluorescent resonance energy transfer (FRET) energy donor and acceptor compound and the energy transfer determined in step iii) is fluorescent resonance energy transfer (FRET).

3. The method of claim 2, wherein the FRET is time resolved FRET.

4. The method of claim 1, wherein the energy donor and acceptor compound are a bioluminescence energy transfer (BRET) energy donor and acceptor compound and the energy transfer determined in step iii) is bioluminescence energy transfer (BRET).

5. The method of claim 1, wherein the energy donor and acceptor compound are an Amplified Luminescent Proximity Homogeneous Assay acceptor and donor bead and the energy transfer determined in step iii) is an energy transfer from a singlet oxygen to an thioxene derivative within the acceptor bead.

6. The method of claim 1, wherein the target antigen is covalently or noncovalently labelled with the energy donor compound.

7. The method of claim 1, wherein the energy donor compound is covalently or noncovalently linked to wheat germ agglutinin (WGA).

8. The method of claim 1, wherein the reporter gene is selected from a gene coding for a fluorescent protein or a gene coding for an enzyme whose catalytic activity can be detected.

9. The method of claim 8, wherein the reporter gene is coding for green fluorescent protein (GFP) or luciferase.

10. The method of claim 1, wherein the target antigen is a cell surface receptor.

11. The method of claim 1, wherein steps iii) and iv) are performed consecutively or simultaneously.

12. The method of claim 1, wherein the target antigen and the response element are part of the NF-κB pathway.

13. The method of claim 12, wherein the response element comprises at least one DNA repeat with a DNA sequence of SEQ ID NO: 1, 2, 3, 4 or 5.

14. The method of claim 12, wherein the response element comprises a DNA sequence of SEQ ID NO 6, 7, 8 or 9.

15. The method of claim 1, wherein the cells are transfected with an expression vector comprising a DNA sequence coding for the reporter gene under the control of the target antigen response element.

16. The method of claim 1, wherein the target antigen is fused to a SNAP tag.

17. The method of claim 16, wherein the target antigen is introduced into the cells by transfection of the cells with a vector that encodes the target antigen.

18. The method of claim 1, wherein the energy donor compound is terbium.

19. The method of claim 1, wherein the cells are grown in the presence of a growth medium or a growth media supplement.

20. The method of claim 1, wherein the test antibody is added at a concentration of at least 40 nM.

21. The method of claim 1, wherein the ratio of the test antibody to the secondary antibody is at least 1:3.

22. The method of claim 1, wherein the cells are mammalian cells.

23. The method of claim 17, wherein the cells are stably transfected and/or transiently transfected with the vector encoding the target antigen.

24. The method of claim 17, wherein the cells are transfected by lipofection.

25. The method of claim 1, wherein the binding to the target antigen and the functionality of the test antibody are measured after incubation of the cell line with the test antibody for at least 4 hours at 37° C.

26. The method of claim 1, wherein determining functionality of the test antibody comprises reducing the volume of the cells before adding a detection reagent to the cells.

* * * * *